(12) United States Patent
Butler et al.

(10) Patent No.: US 11,179,721 B2
(45) Date of Patent: Nov. 23, 2021

(54) MICROFLUIDIC TRAP

(71) Applicant: University of Florida Research Foundation, Inc., Gainesville, FL (US)

(72) Inventors: Jason E. Butler, Gainesville, FL (US); Anthony J. Ladd, Gainesville, FL (US); Mert Arca, Hillsboro, OR (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 478 days.

(21) Appl. No.: 15/746,319

(22) PCT Filed: Jul. 21, 2016

(86) PCT No.: PCT/US2016/043356
§ 371 (c)(1),
(2) Date: Jan. 19, 2018

(87) PCT Pub. No.: WO2017/015468
PCT Pub. Date: Jan. 26, 2017

(65) Prior Publication Data
US 2018/0207639 A1    Jul. 26, 2018

Related U.S. Application Data

(60) Provisional application No. 62/195,137, filed on Jul. 21, 2015.

(51) Int. Cl.
*G01N 27/447*   (2006.01)
*B01L 3/00*   (2006.01)
(Continued)

(52) U.S. Cl.
CPC ..... *B01L 3/502761* (2013.01); *B01L 3/50273* (2013.01); *B01L 3/502715* (2013.01);
(Continued)

(58) Field of Classification Search
None
See application file for complete search history.

(56) References Cited

U.S. PATENT DOCUMENTS

2004/0147043 A1   7/2004   Boer et al.
2004/0256230 A1*  12/2004  Yager ............... G01N 27/44769
                                                           204/450
(Continued)

OTHER PUBLICATIONS

Misra, et al., Mechanics of Vorticella contraction. Biophys. J., 98:2923-2932, 2010.
(Continued)

*Primary Examiner* — Paul S Hyun
(74) *Attorney, Agent, or Firm* — Thomas | Horstemeyer, LLP

(57) ABSTRACT

Provided herein are microfluidic devices that can be configured to generate an electrophoretic flow that is in opposition to a fluid flow through a microcapillary of a microfluidic device provided herein. Also provided herein are methods that include adding an amount of particle to the inlet area of a microfluidic device as provided herein, generating a first fluid flow through a microcapillary of a microfluidic device provided herein; and applying a uniform electric field to the microfluidic device, where the uniform electric field generates an electrophoretic flow that is in opposition to the fluid flow.

7 Claims, 20 Drawing Sheets

(51) Int. Cl.
    *G01N 1/40*    (2006.01)
    *C12Q 1/6816*  (2018.01)
    *C12Q 1/6806*  (2018.01)

(52) U.S. Cl.
    CPC ......... *C12Q 1/6806* (2013.01); *C12Q 1/6816* (2013.01); *G01N 1/4077* (2013.01); B01L 2200/0668 (2013.01); B01L 2300/0838 (2013.01); B01L 2300/16 (2013.01); B01L 2400/0421 (2013.01); B01L 2400/0487 (2013.01); G01N 27/447 (2013.01)

(56) References Cited

U.S. PATENT DOCUMENTS

| | | |
|---|---|---|
| 2005/0224350 A1 | 10/2005 | Sibbett |
| 2006/0292649 A1* | 12/2006 | Cahill ............... B01L 3/502715 435/7.92 |
| 2007/0026421 A1 | 1/2007 | Sundberg |
| 2007/0235335 A1 | 10/2007 | Strand |
| 2008/0087546 A1 | 4/2008 | Strand |
| 2009/0098541 A1 | 4/2009 | Southern |
| 2009/0325153 A1* | 12/2009 | Shuber ................ C12Q 1/6834 435/6.16 |

OTHER PUBLICATIONS

Dickinson, et al., Models for actin polymerization motors. J. Math. Biol., 58:81-103, 2009.

Dickinson, et al., Nematode sperm motility: Nonpolar filament polymerizationmediated by end-tracking motors. Biophys J., 92:622-631, 2007.

Dickinson, et al., Diffusion rate limitations in actin-based propulsionof hard and deformable particles. Biophys. J., 91:1548-1563, 2006.

Liu, et al., Visualizing the strain field in semiflexible polymer networks: Strain fluctuations and nonlinear rheology of f-actin gels. Phys Rev. Lett., 98:198304, 2007.

Brangwynne, et al., Bending dynamics of fluctuating biopolymers probed by automated high-resolution filament tracking. Biophys. J., 93:346-359, 2007.

Lin, et al., Viscoelastic properties of microtubule networks. Macromolecules, 40:7714-7720, 2007.

Brangwynne, et al., Force fluctuations and polymerization dynamics of intracellular microtubules. Proc. Natl. Acad. Sci. U. S. A., 104:16128-16133, 2007.

Brangwynne, et al., Nonequilibrium microtubule fluctuations in a model cytoskeleton. Phys. Rev. Lett., 100:118104, 2008.

Hashimoto, et al., Polymerase chain reaction/ligase detection reaction/hybridization assays using flow-through microfluidic devices for the detection of low-abundant DNA point mutations. Biosens. Bioelectron., 21:1915-1923, 2006.

Guan, et al., Generating highly ordered DNA nanostrand arrays. Proc. Natl. Acad. Sci. U.S.A., 102:18321-18325, 2005.

Felgner, et al., Nonviral strategies for gene therapy. Sci. Am., 276:102107, 1997.

Chan, et al., Adsorption and surface diffusion of DNA oligonucleotides at liquid/solid interfaces. Langmuir, 13:320-329, 1997.

Lee, et al., Evidence for spin coating electrostatic self-assembly of polyelectrolytes. Langmuir, 19:75927596, 2003.

Hoda, et al., Kinetic theory of polyelectrolyte adsorption in shear flow. J. Rheol., 51:799-820, 2007.

Hoda, et al., Brownian dynamics simulations of polyelectrolyte adsorption in shear flow: Effects of solvent quality and charge patterning. J. Chem. Phys., 128:164907, 2008.

Singh, et al., Application of molecular identification tools for Lactobacillus, with a focus on discrimination between closely related species: A review. LWT-Food Science and Technology, 42:448-457, 2009.

Bernardeau, et al., Safety assessment of dairy microorganisms: The *Lactobacillus* genus. International Journal of Food Microbiology, 126:278-285, 2008.

Karger, et al., DNA sequencing by CE. Electrophoresis, 30:S196-S202, 2009.

Slater, et al., DNA gel electrophoresis: The reptation models(s). Electrophoresis, 30:S181-S187, 2009.

Volkmuth, et al., DNA electrophoresis in microlithographic arrays. Nature, 358:600-602, 1992.

Han, et al., Separation of long DNA molecules in a microfabricated entropic trap array. Science, 288:1026-1029, 2000.

Doyle, et al., Self-assembled magnetic matrices for DNA separation chips. Science, 295:2237-2237, 2002.

Tseng, et al., Nanoparticle-filled capillary electrophoresis for the separation of long DNA molecules in the presence of hydrodynamic and electrokinetic forces. Electrophoresis, 26:3069-3075, 2005.

Zheng, et al., Counting single DNA molecules in a capillary with radial focusing. Aust. J. Chem., 56:149-153, 2003.

Jendrejack, et al., Stochastic simulations of DNA in flow: Dynamics and the effects of hydrodynamic interactions. J. Chem. Phys., 116:7752-7759, 2002.

Hsieh, et al., Modeling hydrodynamic interaction in Brownian dynamics: simulations of extensional flow of dilute solutions of DNA and polystyrene. J. Non-Newtonian Fluid Mech., 113:147-191, 2003.

Fixman, et al., Simulation of polymer dynamics. I. General theory. J. Chem. Phys.,69:1527-1537, 1978.

Grassia, et al., Computer simulations of Brownian motion of complex systems. J. Fluid Mech., 282:373-403, 1995.

Kekre, et al., Comparison of lattice-Boltzmann and Brownian-dynamics simulations of polymer migration in confined flows. Phys. Rev. E, 82:011802, 2010.

Staben, et al., Motion of a particle between two parallel plane walls in low-Reynolds-number Poiseuille flow. Phys. Fluids, 15:1711-1733, 2003.

Liron, et al., Stokes flow for a Stokeslet between two parallel flat plates. J. Eng. Math., 10:287-303, 1976.

Swan, et al., Simulation of hydrodynamically interacting particles near a no-slip boundary. Phys. Fluids, 19:113306, 2007.

Ennis, et al., Electrophoretic mobility of a semi-dilute suspension of sphericalparticles with thick double layers and low zeta potentials. J. Colloid Interface Sci., 185:157-173, 1997.

Manning, Limiting laws and counterion condensation in polyelectrolyte solutions.I. Colligative properties. J. Chem. Phys., 51:924, 1969.

Doyle, et al., Dynamics of a tethered polymer in shear flow.Phys. Rev. Lett., 84:4769-4772, 2000.

Chou, et al., Sorting biomolecules with microdevices. Electrophoresis, 21:81-90, 2000.

Kishino, et al., Force measurements by micromanipulation of a single actin filament by glass needles. Nature, 334:74-76, 1988.

Perkins, et al., Relaxation of a single DNA molecule observed by optical microscopy. Science, 264:822-826, 1994.

Hur, et al., Dynamics of dilute and semidilute DNA solutions in the start-up of shear flow. J. Rheol., 45:421-450, 2001.

Wong, et al., Deformation of DNA molecules by hydrodynamic focusing. J. Fluid Mech., 497:55-65, 2003.

Lyon, et al., A dual-beam optical microscope for obsrvation and cleavage of single DNA molecules. Anal. Chem., 70:1743-1748, 1998.

Sia, et al., Microfluidic devices fabricated in poly(dimethylsiloxane) for biological studies. Electrophoresis, 24:3563-3576, 2003.

Silvera-Batista, et al., Long-term improvements to photoluminescence and dispersion stability by flowing SDS-SWNT suspensions through microfluidic channels. J. Am. Chem. Soc., 131:12721-12728, 2009.

Liao, et al., Conformation dependence of DNA electrophoretic mobility in a converging channel. Electrophoresis, 31:2813-2821, 2010.

Nkodo, et al., Diffusion coefficient of DNA molecules during free solution electrophoresis. Electrophoresis, 22:2424-2432, 2001.

Borrego, et al., Graduation rates, grade-point average, and changes of major of female and minority students entering engineering 35th ASEE/IEEE Frontiers in Education Conference, 2005.

(56) References Cited

OTHER PUBLICATIONS

Hipel, et al., The internationalization of engineering education—a tale of two countries. IEEE Trans. Systems, Man, and Cybernetics—Pt C: App. & Rev., 33:137, 2003.
Jackson, Globalization, internationalization, and short-term stays abroad. Int. J.Intercultural Rel., 32:349, 2008.
Hayward, Internationalization of US Higher Education. American Council ofEducation preliminary status report, 2000.
Dilli, et al., A new pedagogy in electrical and computer engineering: An experimental and conceptual approach. Frontiers in Education Conference I, 2002.
Leifer, An active learning design project for a junior-level kinematics and dynamicsclass. Frontiers in Education Conference I, 2002.
Matsubara, et al., Development of virtual learning environment for discovery learning in school education. Systems and Computers in Japan, 33:61, 2002.
Tai, et al., Planning early for careers in science. Science, 312:1143-1144, 2006.
Ladd, et al., A symplectic integration method for elastic filaments. J. Chem. Phys., 130:124909, 2009.
Ladd, et al., Comparison of the static and dynamic properties of a semiflexible polymer using lattice-Boltzmann and Brownian-dynamics simulations. Phys. Rev. E, 80:036704, 2009.
Lettieri, et al., A novel microfluidic concept for bioanalysis using freely moving beads trapped in recirculating flows, Lab on a Chip, 2003, 3, 34-39.
Jellema, et al., Charge-based particle separation in microfluidic devices using combined hydrodynamic and electrokinetic effects, Lab on a Chip, 2009, 9, 1914-1925.
Lettieri, et al., in Micro Total Analysis Systems 2003, ed. M. A. Northrup, K. F. Jensen and D. J. Harrison, Transducers Research Foundation Inc., Squaw Valley, California, USA, 2003, pp. 737-740.
Salentijn, et al., DNA Purification in Continuous Nanoliter Flows Using Flow-Induced Electrokinetic Trapping: Influence of Ionic Strength and Chip Conditioning, Proceedings of the 15th International Conference on Miniaturized Systems for Chemistry and Life Sciences, Oct. 2-6, 2011, Seattle, Washington, USA, 987-989.
Takamura, et al., in Micro Total Analysis Systems, ed. Y. Baba, S. Shoji and A. Van den Berg, Kluwer Academic Publishers, Nara, Japan, 2002, pp. 317-319.
Tomizawa, et al., Trapping probability analysis of a DNA trap using electric and hydrodrag force fields in tapered microchannels, Physical Review E 79, 051902, 2009.
Lin, et al., Microfluidics and Nanofluidics, 2011, 10, 481-511.
Han, et al., Science, 2000, 288, 1026-1029.
Martel, et al. Scientific reports, 2015, 5, 1-5.
Ugaz, et al., Microfluidic Technologies for Miniaturized Analysis-Systems, Springer US, 2007, pp. 393-438.
Shendruk, et al., Curr. Op. Coll. Inter. Sci., 2012,17, 74-82.
Viovy, Rev. Mod. Phys., 2000, 72, 813-872.
Perkins, et al., Science, 1997, 276, 2016-2021.
Smith, et al., Science, 1998, 281, 1335-1340.
Shaqfeh, et al., J. Non-Newton. Fluid, 2005, 130, 1-28.
Chen, et al., Macromolecules, 2007, 40, 5978-5984.
Jendrejack, et al., J. Chem. Phys, 2003, 119, 1165-1173.
Jendrejack, et al., Phys. Rev. Lett., 2003, 91, 038102.
Jendrejack, et al., The Journal of Chemical Physics, 2004, 120, 2513-2529.
Ma, et al., Phys. Fluids., 2005, 17, 083103.
Stone, et al., Annu Rev Fluid Mech, 2004, 36, 381-411.
Stroock, et al., Science, 2002, 295, 647-651.
Liu, et al., Microelectromechanical Systems, Journal of, 2000, 9,190-197.
Nguyen, et al., Journal of Micromechanics and Microengineering, 2005,15, R1.
Zheng, et al., Anal. Chem., 2002, 74, 4536-4547.
Zheng, et al., Anal. Chem., 2003, 75, 3675-3680.
Arca, et al., Soft Matter, 2015, 11, 4375-4382.
Wang, et al., Analytical Chemistry, 2005, 77, 4293-4299.
Usta, et al., Phys. Rev. Lett., 2007, 98, 098301.
Rekre, et al., Phys. Rev. E, 2010, 82, 050803.
Butler, et al., Phys. Fluids, 2007, 19, 113101.
Leong, et al., Industrial Laser Solutions, 2004, 19, 1-5.
Yeung, Dynamics of single biomolecules in free solution. Annu. Rev. Phys. Chem.,55:97-126, 2004.
Hernandez-Ortiz, et al., Cross-stream-line migration in confined flowing polymer solutions: Theory and simulation. Phys. Fluids,18:123101, 2006.
Usta, et al., Flow-induced migration of polymers in dilute solution. Phys. Fluids, 18:031703, 2006.
Fang, et al., DNA configurations and concentration in shearing flow near a glass surface in a microchannel. J. Rheol., 49:127-138, 2005.
Saintillan, et al., Effect of flexibility on the shear-induced migration of short-chain polymers in parabolic channel flow. J. Fluid Mech., 557:297-306, 2006.
Fair, et al., Electrophoresis of dumbbell-like colloidal particles. Int. J. Multiphase Flow, 16:663-679, 1990.
Solomentsev, et al., Electrophoresis of slender particles. J. Fluid Mech., 279:197-215, 1994.
Barrat, et al., Theory of polyelectrolyte solutions. Adv. Chem. Phys., 94:1-66, 1994.
Manning, Limiting laws and counterion condensation in polyelectrolyte solutions.7. Electrophoretic mobility and conductance. J. Phys. Chem., 85:1506-1515, 1981.
Stellwagen, et al., Electrophoresis of DNA in agarose gels, polyacrylamide gels and infree solution. Electrophoresis, 30:S188-S195, 2009.
Allison, et al., A commentary on the screened-Oseen, counterioncondensationformalism of polyion electrophoresis. Biophys. J., 78:121-124, 2000.
Long, et al., Simultaneous action of electric fields and nonelectric forces on a polyelectrolyte: motion and deformation. Phys. Rev. Lett, 76:3858-3861, 1996.
Long, et al., A note on the screening of hydrodynamic interactions, in electrophoresis, and in porous media. Eur. Phys. J. E, 4:29-32, 2001.
Chen, et al., Electrophoresis and sedimentation of charged fibers. J. Coll. Int. Sci., 180:466-477, 1996.
Han, et al., Orientation distribution and electrophoretic motions of rodlike particles in a capillary. J. Coll. Int. Sci., 177:132-142, 1996.
Teles, et al., Trends in DNA biosensors. Talanta, 77:606-623, 2008.
Chopra, et al., Brownian dynamics simulations of isolated polymer molecules in shear flow near adsorbing and nonadsorbing surfaces J. Rheol., 46:831862, 2002.
Zhang, et al., PCR microfluidic devices for DNA amplification. Biotechnol. Adv., 24:243284, 2006.
International Search Report for PCT/US16/43356 dated Oct. 17, 2016.

* cited by examiner

(a) Entry Region  Exit Region t = 0 min t = 1 min t = 5 min

MICROFLUIDIC TRAP

CROSS-REFERENCE TO RELATED APPLICATIONS

This application is the 35 U.S.C. § 371 national stage application of PCT Application No. PCT/US2016/043356, filed Jul. 21, 2017, where the PCT claims the benefit of and priority to U.S. Provisional Patent Application No. 62/195,137, filed on Jul. 21, 2015, entitled "MICROFLUIDIC TRAP," both of which are herein incorporated by reference in their entirety.

STATEMENT REGARDING FEDERALLY SPONSORED RESEARCH OR DEVELOPMENT

This invention was made with government support under grant number 1067072 awarded by the National Science Foundation. The government has certain rights to this invention.

BACKGROUND

Separation and concentration of nucleic acids and polynucleotides can play significant roles in many research, diagnostic, forensic, and clinical applications. As such, there exists a need for improved devices and techniques for separating and/or concentrating nucleic acids and polynucleotides.

SUMMARY

Provided herein are microfluidic devices that can contain an inlet area, where the inlet area has an entry region; and a microcapillary, where the microcapillary can be fluidly coupled to the entry region of the inlet area and the exit region of the outlet area, where the microfluidic device can be configured to generate an electrophoretic flow that can be in opposition to a fluid flow through the microcapillary. The particle can be concentrated at the entry region when the electrophoretic flow is in opposition to a fluid flow through the microcapillary. The width of the microcapillary can range from about 0.1 µm to about 2 mm. The length of the microcapillary can range from about 100 µm to about 1 m. The inlet area can have a width that can be at least greater than the width of the microcapillary. The inlet area can have a length ranging from about 0.1 µm to about 1 m. The inlet area can have a height ranging from about 0.1 µm to about 500 µm. The microcapillary can be coated with a neutral compound or neutral polymer. A capture molecule can be coupled to or physically attached to a region of the reservoir and/or microcapillary. The microfluidic devices provided herein can further include an outlet area, where the outlet area can have an exit region and where the microcapillary can be fluidly coupled to the exit region of the outlet area. The inlet area can be part of the microcapillary. The outlet area can be part of the microcapillary. The outlet area can have a width that can be at least greater than the width of the microcapillary. The outlet area can have a length ranging from about 0.1 µm to about 1 m. The outlet area can have a height ranging from about 0.1 µm to about 500 µm.

Also provided herein are multilayered microfluidic device including one or more microfluidic devices as provided herein.

Also provided herein are methods that can include the steps of adding an amount of particle to the inlet area of a microfluidic device as provided herein; generating a first fluid flow through a microcapillary of the microfluidic device; and applying a uniform electric field to the microfluidic device, where the uniform electric field generates an electrophoretic flow that is in opposition to the fluid flow. The method can further include the step of concentrating the particle at the entry region of the inlet area. The particle can be a nucleic acid or polynucleotide. The method can further include the step of quantitating the amount of particle concentrated at the entry region of the inlet area. The concentrated particle can be collected from the microfluidic device. The concentrated particle can be collected from the microfluidic device by applying a second fluid flow to the inlet region and/or inlet area that is not parallel to the first fluid flow. The second fluid flow can be about perpendicular to the first fluid flow.

Also provided herein are methods that can include the step of adding an amount of particle to the inlet area of a multilayered microfluidic device as provided herein, generating a first fluid flow through the microcapillary of the microfluidic device; and applying a uniform electric field to the microfluidic device, where the uniform electric field generates an electrophoretic flow that is in opposition to the fluid flow. The method can further include the step of concentrating the particle at the entry region of the inlet area. The particle can be a nucleic acid or polynucleotide. The method can further include the step of quantitating the amount of particle concentrated at the entry region of the inlet area. The concentrated particle can be collected from the microfluidic device. The concentrated particle can be collected from the microfluidic device by applying a second fluid flow to the inlet region and/or inlet area that is not parallel to the first fluid flow. The second fluid flow can be about perpendicular to the first fluid flow.

BRIEF DESCRIPTION OF THE DRAWINGS

Further aspects of the present disclosure will be readily appreciated upon review of the detailed description of its various embodiments, described below, when taken in conjunction with the accompanying drawings.

DETAILED DESCRIPTION

Figure 1:
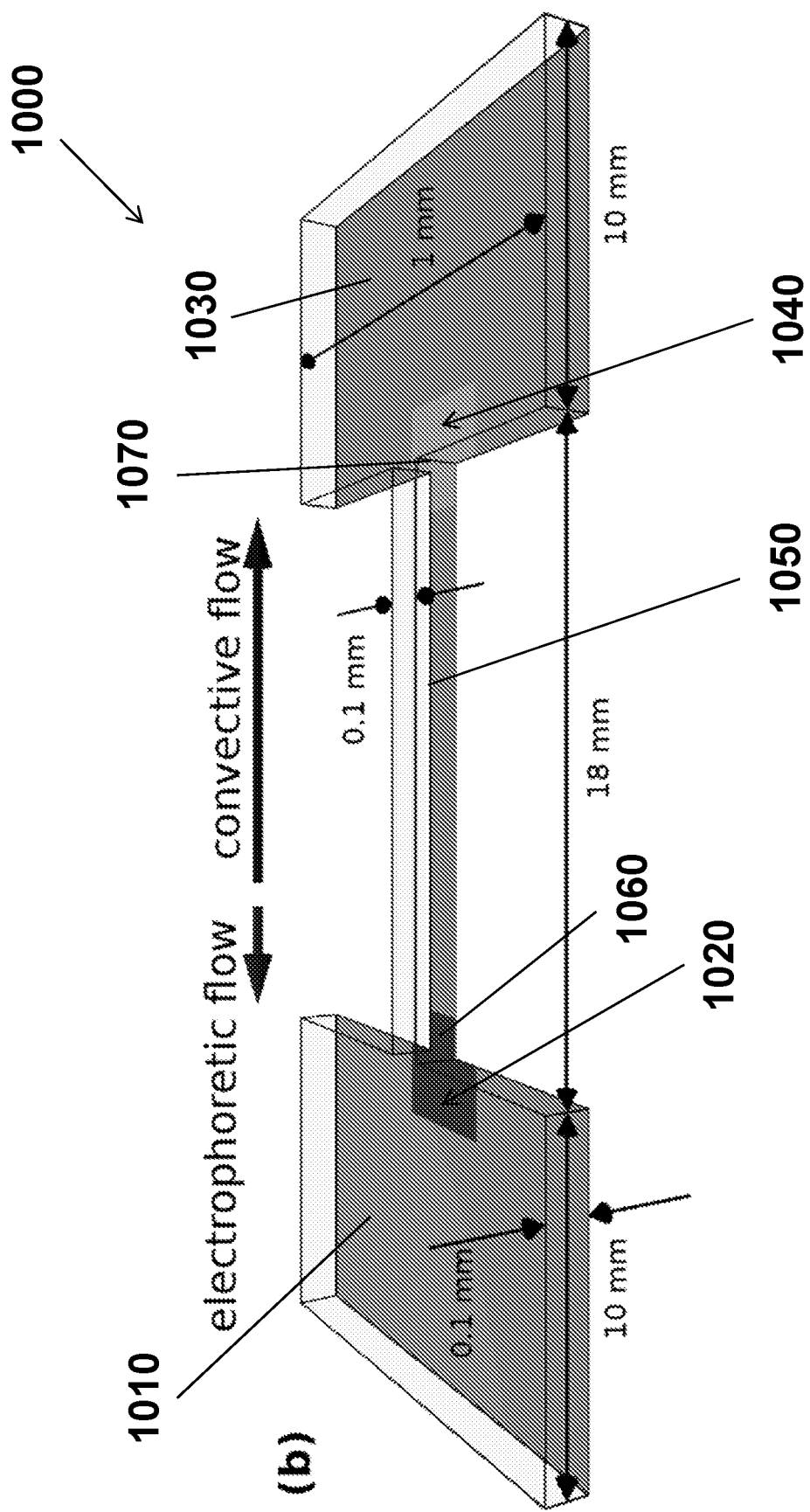
FIG. 1 shows one embodiment of a microfluidic trap.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of molecular biology, microbiology, nanotechnology, organic chemistry, biochemistry, botany and the like, which are within the skill of the art. Such techniques are explained fully in the literature.

Definitions

As used herein, "about," "approximately," and the like, when used in connection with a numerical variable, generally refers to the value of the variable and to all values of the variable that are within the experimental error (e.g., within the 95% confidence interval for the mean) or within +/−10% of the indicated value, whichever is greater.

As used herein, "deoxyribonucleic acid (DNA)" and "ribonucleic acid (RNA)" generally refer to any polyribonucleotide or polydeoxribonucleotide, which may be unmodified RNA or DNA or modified RNA or DNA. RNA may be in the form of a tRNA (transfer RNA), snRNA (small nuclear RNA), rRNA (ribosomal RNA), mRNA (messenger RNA), anti-sense RNA, RNAi (RNA interference construct), siRNA (short interfering RNA), or ribozymes.

As used herein, "polynucleotide" refers to an oligomer and polymers of nucleotides.

As used herein, "particle" refers to any object that is anisotropic in either shape or charge distribution, including particles, nanoparticles, soft spherical and non-spherical objects, and molecules, that are electrophoretic and/or deformable. Particles can include, without limitation, nucleic acids (e.g. DNA and RNA), proteins, and carbon nanotubes.

As used herein, "inlet area" refers to the three dimensional area adjacent to and/or surrounding the inlet to the microfluidic channel. The inlet area can be part or all of a reservoir that can contain a fluid. The inlet area can be part of a microcapillary. The inlet area can be part of any other container, capillary, microcapillary, tube, pipeline that can feed into the microcapillary.

As used herein, "outlet area" refers to the three dimensional area adjacent to and/or surrounding the outlet to the microfluidic channel. The outlet area can be part or all of a reservoir that can contain a fluid. The outlet area can be part of a microcapillary. The outlet area can be part of any other container, capillary, microcapillary, tube, pipeline that can receive fluid flow from the microcapillary.

As used herein, "capture molecule" refers to a molecule that is configured to specifically bind one or more biomarker molecules of interest. A capture molecule can be a nucleotides, antibody, antigen, apatmer, affibody, polypeptides, peptides, or combinations thereof that specifically bind one or more biomarkers of interest.

As used herein "attached" as applied to capture molecules of an array refers to a covalent interaction or bond between a molecule on the surface of the support and the capture molecule so as to immobilize the capture molecule on the surface of the support.

As used herein "operatively-linked" as applied to capture molecules of an array refers to a non-covalent interaction between the surface of the support and the capture molecule so as to immobilize the capture molecule on the surface of the support. Such non-covalent interactions include by are not limited to, entrapment by the surface substrate, ionic bonds, electrostatic interactions, van der Walls forces, dipole-dipole interactions, dipole-induced-dipole interactions, London dispersion forces, hydrogen bonding, halogen bonding, electromagnetic interactions, $\pi$-$\pi$ interactions, cation-$\pi$ interactions, anion-$\pi$ interactions, polar $\pi$-interactions, and hydrophobic effects.

As used herein, "multilayered microfluidic device" refers to a microfluidic device that contains more than one individual microfluidic devices, where the individual microfluidic devices can be fluidly coupled and/or physically coupled to one or more other microfluidic devices of the multilayered microfluidic device and where the individual microfluidic devices are arranged within the multilayered microfluidic device such that there is more than one level of microfluidic devices in any given dimension.

Discussion

The transport of DNA through microfluidic devices relies primarily on electric fields, and less often on pressure-driven flows. Numerous studies have examined the detailed transport under a wide range of conditions for both types of fields; extensive reviews are available regarding the electrophoretic motion of DNA and detailed studies of the conformation and transport of DNA in shear flows are available For capillaries much larger than the DNA, the DNA remains well-distributed across the transverse direction save for an excluded volume interaction with the walls and, in the case of pressure-driven flow, a small depletion layer caused by hydrodynamic effects.

To meet the needs of greater control and manipulation of DNA within microfluidic channels, researchers have introduced higher-dimensional features to the devices. To weaken axial dispersion, channels have been curved to introduce a secondary, transverse flow that mixes the DNA and introducing steps into a channel can separate DNA by length. Although diffusion tends to distribute molecules uniformly across a capillary, hydrodynamic flows, particularly when combined with an electric field, can produce strongly inhomogeneous distributions within a single cross-section. A flow field by itself produces a degree of focusing towards the center of the capillary, which hinders the detection of proteins and DNA fragments by reducing the concentration at the walls of the capillary where the biomarkers can be located and thus current microfluidic biopolymer separation devices suffer from inefficient and often poor performance.

With that said, described herein are microfluidic devices that can concentrate and/or trap a particle, including without limitation biopolymers, within a specific region of a microcapillary of a microfluidic device using a uniform electric field that can act in opposition to a fluid flow through the microcapillary. The microfluidic devices described herein can be used in series with other devices and techniques that require a specific population and/or concentration of particles. Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description, and be within the scope of the present disclosure.

Microfluidic Particle Trap

Described herein are microfluidic devices capable of concentrating and/or trapping a particle in a region within the microfluidic device. The microfluidic devices described herein are configured to generate and/or contain a fluid flow that is in opposition to an electric field, which can produce a hydrodynamic flow coupled with a recirculation flow within the microfluidic device that concentrates the particle in a region within the microfluidic device.

With the general concept described, attention is directed to FIG. 1, which shows one embodiment of a microfluidic trap 1000. The microfluidic trap 1000 can have an inlet area 1010, where the inlet area 1010 can have an entry region 1020. The entry region 1020 is the three dimensional area within the inlet area 1010 where the particle can concentrate. The microfluidic trap 1000 can have an outlet area 1030, where the outlet area 1030 can have an exit region 1040. The microfluidic trap 1000 can further have a microcapillary 1050, where one end of the microcapillary 1050 is fluidly coupled and/or physically coupled to the entry region 1020 of the inlet area 1010 and the other end of the microcapillary 1050 is fluidly coupled to and/or physically coupled to the exit region 1040 of the outlet area 1030. The point where the microcapillary 1050 meets the entry region 1020 can be referred to as the microcapillary inlet 1060. The point where the microcapillary 1050 meets the exit region 1040 can be referred to as the microcapillary outlet 1070.

The microcapillary 1050 and/or the inlet area 1010 and/or outlet area 1030 can be coated, either partially or completely, with a suitable neutral compound or polymer. Suitable neutral polymers include, but are not limited to, polyvinylpyrrolidone (PVP), polyvinyl alcohol (PVA), methyl cellulose, and non-cross-linked polyacrylamide. The coating can suppress electroosmosis and prevent electro osmotic flow. Electroosmotic flow can allow the particle to escape concentration and/or trapping by the microfluidic trap 1000 because the electroosmotic flow generated can be larger than the velocity of the electrophoretic flow. The microcapillary 1050 and/or the inlet area 1010 and/or outlet area 1030 can further contain one or more capture molecules, such as a nucleic acid that is complementary to a nucleic acid of interest, an antibody or aptamer, or other specific binding partner to a particle of interest.

The microfluidic trap 1000 can be configured to generate an electrophoretic flow that is in opposition to a fluid flow through the microcapillary 1050. Devices and mechanisms to generate a fluid flow through a microfluidic device are generally known to those of skill in the art. Devices and mechanisms to generally apply a current through a microfluidic device are generally known to those of skill in the art. When an electrophoretic flow is generated in the microfluidic trap 1000 in opposition to a fluid flow in the microfluidic trap 1000, a particle, which is oriented at an angle to the fluid flow prior to the generation of an electrophoretic flow, the particle can be driven to the walls of the microcapillary 1050 and then recirculated back towards the entry region 1060. Without being bound by theory, it is believed that the net orientation of particles drives a flux of the particles perpendicular to the field lines (See e.g. FIGS. 4 and 5), which concentrates the particle at a stagnation point/region within the microcapillary 1050 and/or entry region 1020.

The width of the microcapillary can be greater than about 0.1 µm. In some embodiments, the width of the microcapillary 1050 can range from about 0.1 µm to about 2 mm. The microcapillary can be any suitable and/or desired length. In some embodiments, the length of the microcapillary can range from about 100 µm to about 1 m or greater. It will be appreciated that the length and width of the microcapillary 1050 can vary according to the size of particle desired to be concentrated and/or trapped. By altering the dimensions of the microcapillary 1050 it can be possible to tune the size and/or type of particle being concentrated and/or trapped. The microcapillary 1050 can be uniform in dimensions along its length. In other embodiments, the microcapillary 1050 can be tapered at one or both ends. In further embodiments, the microcapillary 1050 can contain one or more steps where the width and/or height of the microcapillary 1050 changes (increases or decreases) abruptly to generate a step form in the shape of the microcapillary 1050. These changes in dimensions can further allow a user to tune the size and/or type of particle being concentrated/trapped. These changes in dimensions can also allow a user to tune the stagnation point where the particle is concentrated and/or trapped.

The inlet area 1010 can have a width that is at least greater than the width of the microcapillary 1050. In some embodiments, the inlet area 1010 can have a width ranging from about 1 mm to about 100 mm. The inlet area 1010 can have any suitable and/or desirable length greater than 0. In some embodiments, the length of the inlet area 1010 is greater than 0.1 µm. In other embodiments, the inlet area 1010 can have a length ranging from about 0.1 µm to about 1 m. The height of the inlet area 1010 can be any suitable and/or desired height greater than 0. In some embodiments, the inlet area 1010 can have a height ranging from about 1 µm to about 500 µm.

The outlet area 1030 can have a width that is at least greater than the width of the microcapillary 1050. In some embodiments, the outlet area 1030 can have a width ranging from about 1 mm to about 100 mm. The outlet area 1030 can have any suitable and/or desirable length greater than 0. In some embodiments, the length of the outlet area 1030 is greater than 0.1 µm. In other embodiments, the outlet area 1030 can have a length ranging from about 0.1 µm to about 1 m. The height of the outlet area 1030 can be any suitable and/or desired height greater than 0. In some embodiments, the outlet area 1030 can have a height ranging from about 1 µm to about 500 µm.

Figure 18A:
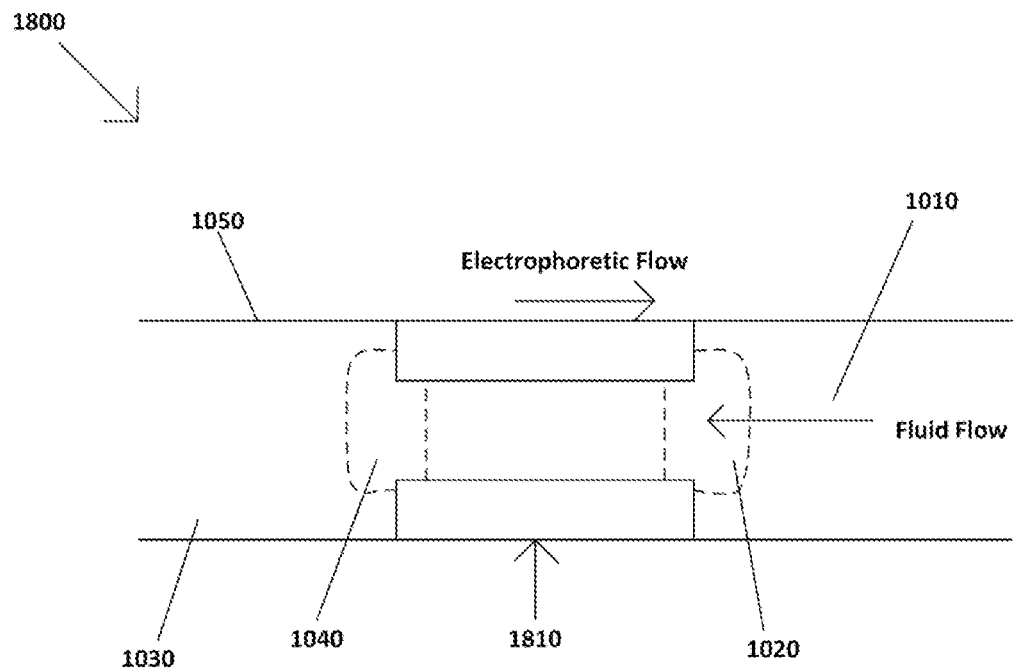
FIGS. 18A-18B show embodiments of a microfluidic trap where an inlet area and/or an outlet area are part of a microcapillary.
Figure 18B:
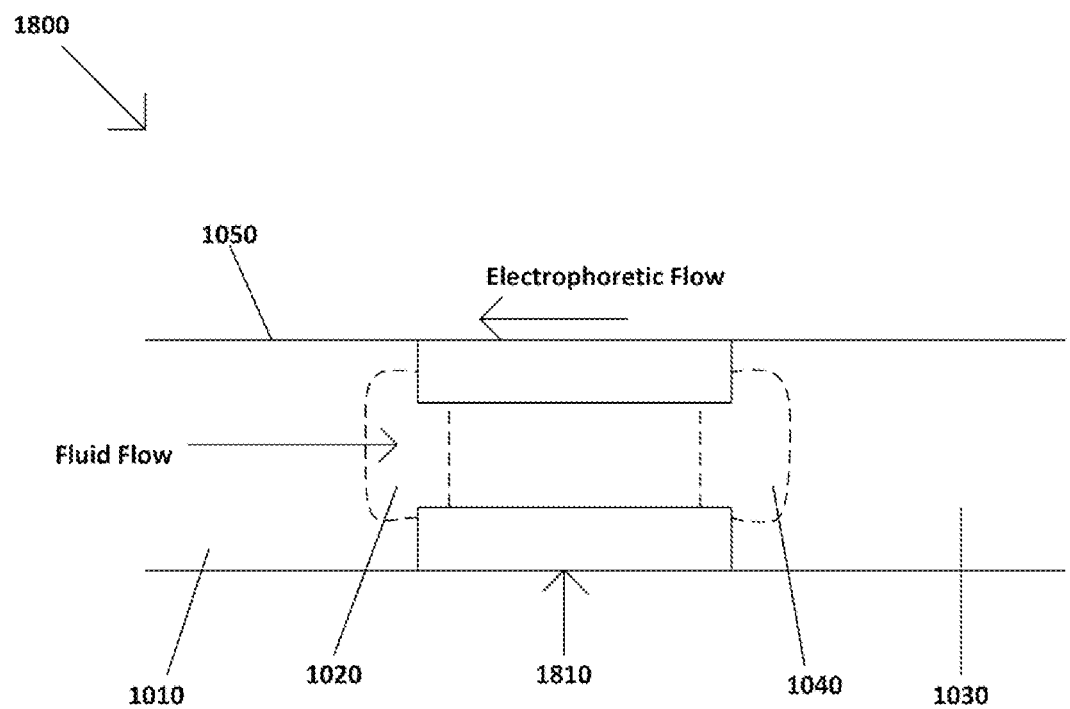

In some embodiments, a microfluidic trap can include a microcapillary that is constricted in one or more places along its length. In other words, in one or more places along its length, the cross-sectional area of the microcapillary is decreased. With this in mind, attention is directed to FIGS. 18A-18B, which show embodiments of a microfluidic trap 1800 where an inlet area 1010 and/or an outlet area 1030 are part of a microcapillary 1050. The constriction 1810 can generate an inlet area 1010 and/or outlet area 1030 within the microcapillary 1050. The length of the constriction 1810 can be greater than 0 but less than the entire length of the microcapillary 1050.

Figure 19A:
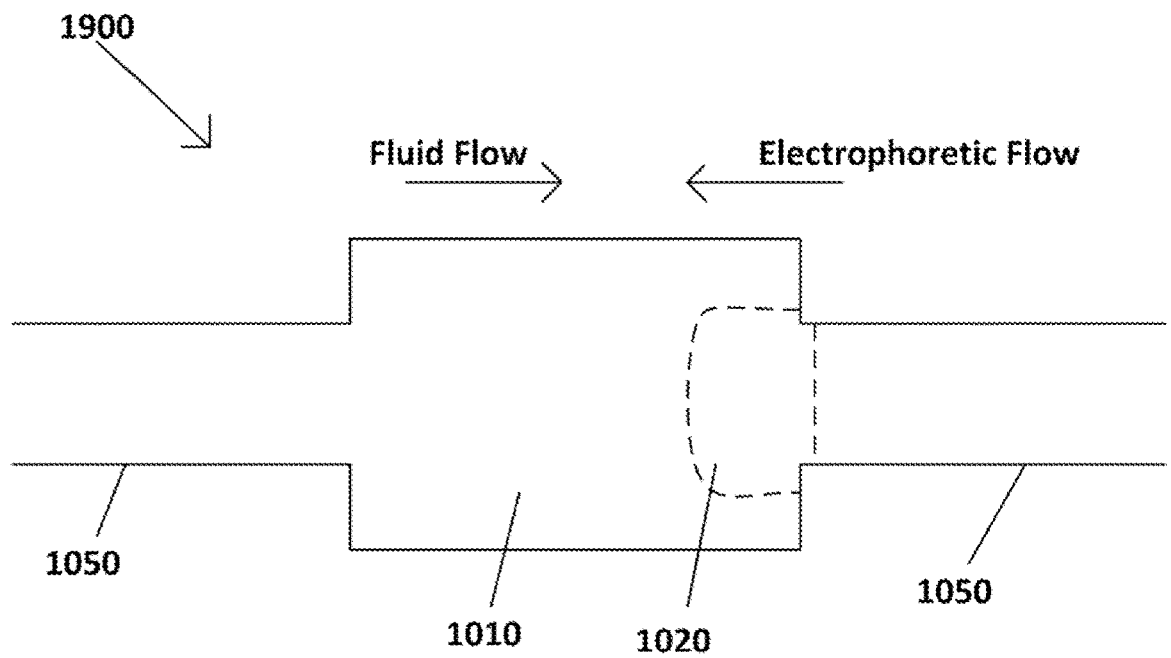
FIGS. 19A-19B show embodiments of a microfluidic trap that does not contain an outlet area.
Figure 19B:
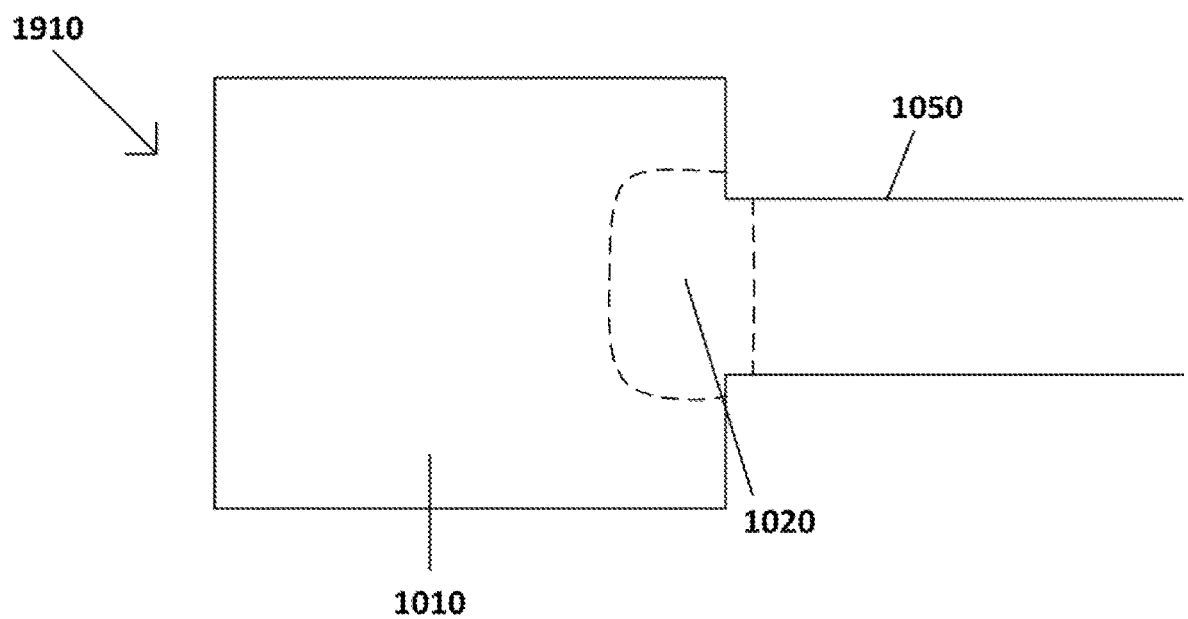

In other embodiments, the microfluidic trap does not contain an outlet area. With that said FIGS. 19A-19B show embodiments of a microfluidic trap 1900, 1910 that does not contain an outlet area. In these embodiments, the desired particles are concentrated at the entry region 1020 of the microfluidic trap 1900, 1910. The concentrated particles can be analyzed at that point or otherwise collected from the microfluidic trap 1900, 1910.

Figure 20:
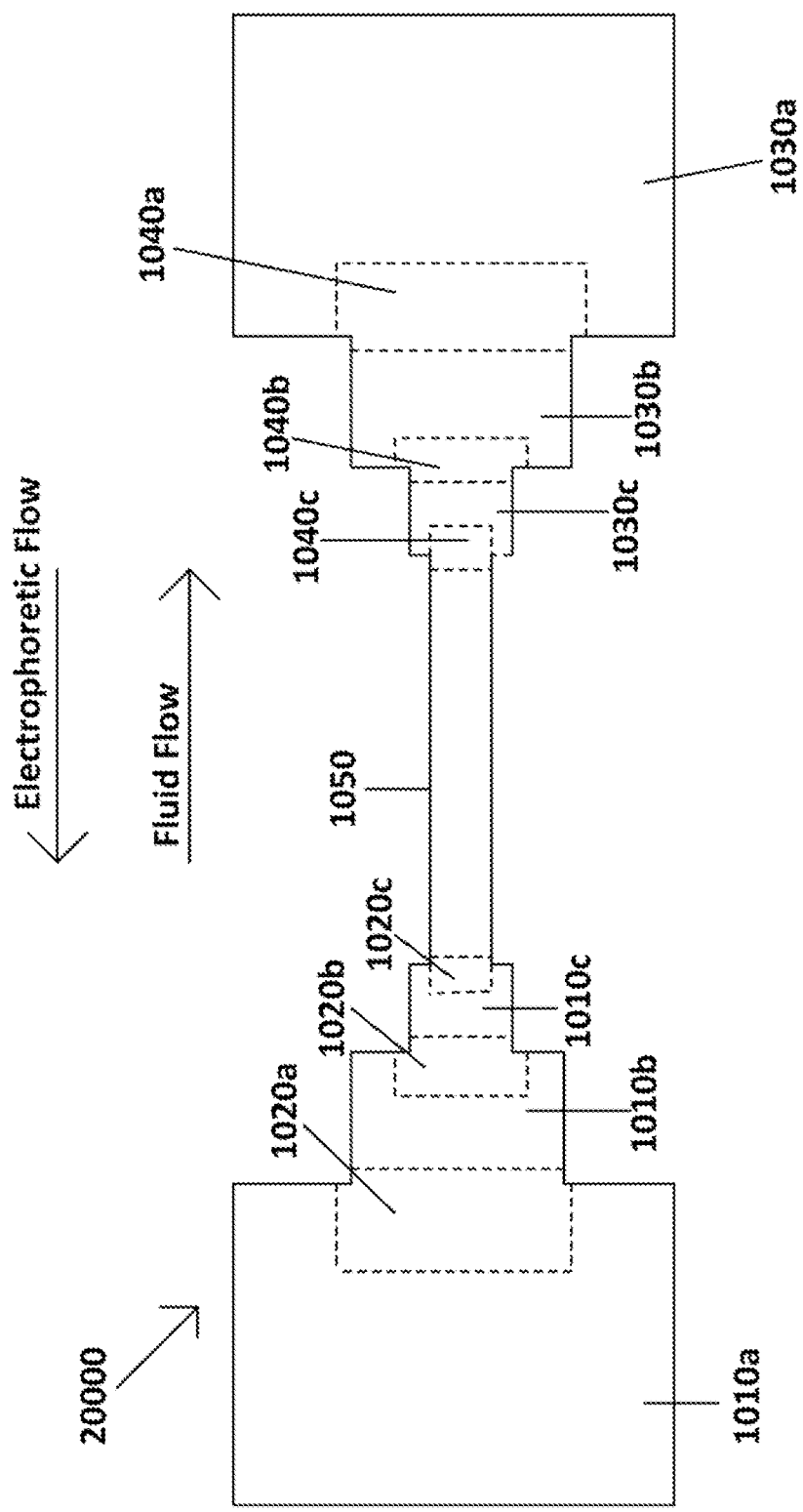
FIG. 20 shows an embodiment of a microfluidic trap having multiple inlet areas and outlet areas.

The microfluidic trap can contain multiple inlet areas and/or outlet areas. With that said, FIG. 20 shows an embodiment of a microfluidic trap having multiple inlet areas and outlet areas. By generating step-wise or tapered changes in the width of the inlet area 1010, outlet area 1030 and/or microcapillary 1050, the particle can be concentrated at one or more of these entry regions 1020 *a,b,c*.

Figure 21:
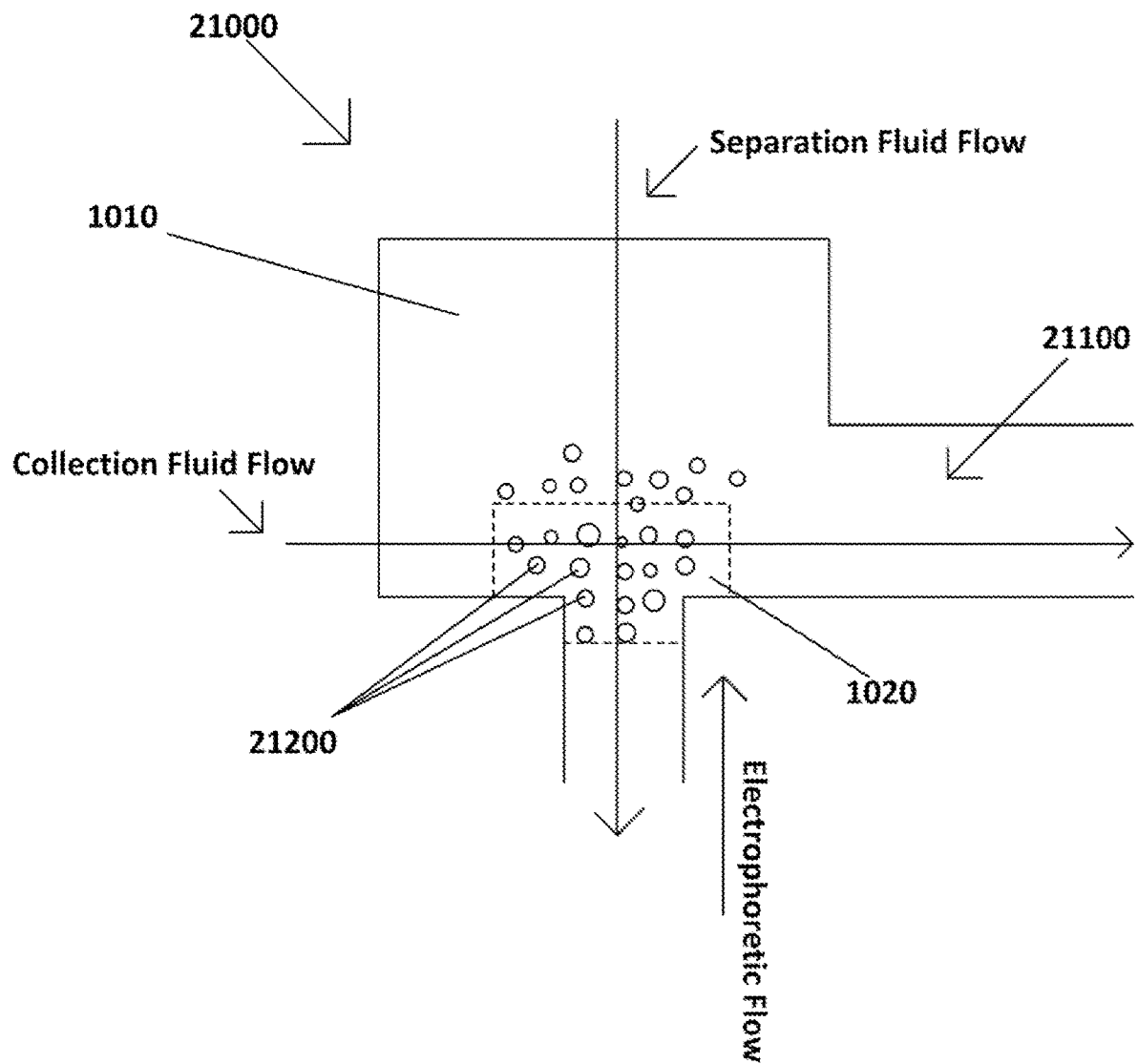
FIG. 21 shows an embodiment of a microfluidic trap configured to collect concentrated particles via a fluid flow that is not parallel to the fluid flow used to drive sample particles into the microcapillary.

In some embodiments, it is desirable to collect the concentrated particles and directly transport the concentrated particles into an additional microfluidic device (such as in a multilayered microfluidic device) or other device for further particle processing or analysis. With that said, FIG. 21 shows an embodiment of a microfluidic trap 21000 configured to collect concentrated particles 21200 via a fluid flow (collection fluid flow) that is not parallel to the fluid flow used to drive sample particles into the microcapillary (separation fluid flow). The collection fluid flow can be applied at any angle that is not parallel to the separation fluid flow. The inlet area 1010 can be configured to contain a collection port 21100 that can be fluidly and/or physically coupled to an additional microfluidic or other device. The collection fluid flow can drive the collected particles into the collection port 21100 and into the additional microfluidic or other device for further processing and/or analysis.

The microfluidic trap described herein can further contain one or more detectors configured to detect one or more of the concentrated/trapped particles. Suitable detectors are generally known to those of ordinary skill in the art. The detector can be placed at any point in the microfluidic trap. In some embodiments, the detector can be placed at an entry region and/or collection point (also referred to herein as the stagnation point).

Methods of Using the Microfluidic Trap

Described herein are methods of using the microfluidic trap described herein. The microfluidic trap described herein can be used to concentrate and/or trap a particle at a particular point or region within the microfluidic trap. By applying an opposing fluid flow and electric fields to a solution containing an amount of a particle in the microcapillary, the particle can be concentrated and/or trapped at a particular point or region within the microfluidic trap.

Particles contained in a pressure-driven fluid flow can orient themselves at an angle to the fluid flow. When an axial electric field is applied to the fluid, the net orientation of the particle can drive a flux of molecule perpendicular to the field lines. This is demonstrated in FIG. 4. Modest pressure drops (i.e. less than about 1 cm) and voltages (less than about 100 V) acting in opposition from one another, can drive a particle (e.g. DNA) to the walls of a microcapillary in a distance of less than 1 cm. The particle can become focused in a thin sheet (about 1 µm or less thick) next to the wall of the microcapillary. The thin layer of particle can contain almost, if not all of the particle present in the capillary. The thin layer of particle can be driven back against the fluid flow by the electrophoretic flow generated by the opposing electric field. By tuning the electric field to the fluid flow, a stagnation point can be generated at the microcapillary inlet (or other suitable region within the microfluidic trap). The stagnation point is where the particle can be concentrated. Because the particle is present and concentrated in a known area in the microfluidic trap, it is readily available for detection, extraction, or binding to a capture molecule located at or in the region of the stagnation point.

The method of concentrating and/or trapping a particle using a microfluidic trap as substantially described herein can contain the steps of adding an amount of particle to the inlet area of a microfluidic device as substantially described herein, generating a fluid flow through the microcapillary of the microfluidic device and applying an electric field to the microfluidic device, where the electric field generates an electrophoretic flow that is in opposition to the fluid flow. The rate of fluid flow can range according to, inter alia, the dimensions of the microcapillary, the type of particle being concentrated and/or trapped, and the size of the particle being concentrated and/or trapped. In some embodiments, the rate of fluid flow can range from about 1 µm/s to about 500 mm/s. The fluid flow can be pulsed (i.e. repeated on/off cycles). The voltage of the electric field can vary according to, inter alia, the dimensions of the microcapillary, the type of particle being concentrated and/or trapped, and the size of the particle being concentrated and/or trapped. In some embodiments, the voltage can range from about 1 V/cm to about 1 kV/cm. The electric field can be a uniform electric field. In some embodiments, the electric field can be applied in pulses (i.e. repeated on/off cycles). The electric field can be applied for any suitable length of time. It will be appreciated that the length of time that the electric field is applied for can vary according to, inter alia, the dimensions of the microcapillary, the type of particle being concentrated and/or trapped, and the size of the particle being concentrated and/or trapped. Determining the appropriate length of time and/or voltage and/or fluid flow rate can be accomplished without undue experimentation by one of ordinary skill in the art.

The fluid flow and electric field can be generated simultaneously within the microfluidic trap. In other embodiments, the fluid flow and the electric field are generated serially from one another. For example, the fluid flow can be generated and allow the particle to enter the microcapillary prior to applying the electric field or the electric field can be applied prior to generating a fluid flow within the microfluidic trap.

The method can further contain the step of concentrating and/or trapping the particle at the entry region of the inlet area of the microfluidic device. The method can further contain the step of quantitating the amount of particle concentrated at the entry region of the inlet area. The method can further contain the step of specifically binding one or more molecules of the particle to one or more capture molecules physically coupled to the microcapillary or inlet region of the microfluidic trap. The method can further contain the step of detecting one or more molecules of the collected particle. Methods of detecting particles are generally known in the art.

The method can further contain the step of collecting (i.e. removing one or more particle molecule from the point of collection) one or molecules of the particle after concentrating and/or trapping the particle within the microfluidic device. Collection of the particle can include without limitation, aspiration, adding/removing an electric field, and/or adding/removing a separation fluid flow (i.e. the fluid flow that drives the particles into the microcapillary for separation under an opposing electric field). In other embodiments, collection of the particle can include applying a collection fluid flow across the collection point (also referred to herein as the stagnation point), where the collection fluid flow is not parallel to the direction of the separation fluid flow. One embodiment that demonstrates collection of the particle using a collection fluid flow is shown in FIG. 20, which is discussed above. The concentrated particle can then be used in downstream methods and techniques generally known to those of ordinary skill in the art. These can include, without limitation, any form of PCR, nucleic acid sequencing, protein sequencing, and liquid chromatography.

The devices described here can be tuned by altering the fluid flow, voltage, and dimensions/configuration of the devices described herein to separate specific particles within a suspension from undesired particles within the same suspension. The desired particles can be concentrated/trapped at the collection point when the fluid flow through the microcapillary is opposed by a uniform electric field. The undesired particles can pass through or not be collected or removed from the microfluidic trap.

The input suspension for separation can be from any source prepared by any suitable method generally known in the art. In some embodiments, the suspension can be a cell lysate that was processed outside of the microfluidic trap or within the microfluidic trap. In other embodiments, the suspension can be a PCR product in the PCR reaction solution. In these embodiments, the device can be used to separate out the desired PCR product from the primers, enzymes, and other components of the PCR reaction solution. In short, the devices and methods described herein can be used to separate any desired particle or group of particles from an undesirable one and, in some embodiments, prepare the solution or otherwise analyze the concentrated desired particle within the device itself.

EXAMPLES

Now having described the embodiments of the present disclosure, in general, the following examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure.

Example 1

Introduction

Microfluidic devices have been developed to detect, concentrate [1], and separate [2, 3] DNA, proteins, and other charged biomolecules. In these devices the concentration within the capillary cross-section is treated as if it were uniform, although in most cases it is not. In this Example it is demonstrated that the non-uniformity in concentration within a microcapillary can be utilized to develop new and more effective devices for manipulating DNA and other charged biopolymers.

The transport of DNA through microfluidic devices relies primarily on electric fields, and less often on pressure-driven flows. Numerous studies have examined the detailed transport under a wide range of conditions for both types of fields; extensive reviews are available regarding the electrophoretic motion of DNA [4-6] and detailed studies of the conformation and transport of DNA in shear flows are available [7-9].

For capillaries much larger than the DNA, the DNA remains well-distributed across the transverse direction save for an excluded volume interaction with the walls and, in the case of pressure-driven flow, a small depletion layer [10] caused by hydrodynamic effects [11-14]. To meet the needs of greater control and manipulation of DNA within microfluidic channels, researchers have introduced higher-dimensional features to the devices [2]. To weaken axial dispersion, channels have been curved to introduce a secondary, transverse flow that mixes the DNA [15-18] and introducing steps into a channel can separate DNA by length [2].

The simultaneous application of parallel flow and electric fields provides another option for exploiting the full space of the capillaries that introduces no, or little, additional complexity to the microchannel. Measurements [19, 20] have demonstrated that using an electric field to move DNA molecules through a straight and uniform channel, while also applying a pressure-gradient to increase the transport rate, results in a net migration transverse to the field lines that focuses the DNA along the center-line of the channel. The rate of the focusing is rapid, as an initially homogeneous suspension of DNA flowing through a channel of size 100×100 microns will focus within seconds upon applying the electric field [21]. Furthermore, a pressure-gradient that reduces the transport rate of the electric field drives a net migration of the DNA towards the bounding walls of the channel.

Here, it is demonstrated how a simple capillary device with a step change in cross-section can be used to concentrate a solution of DNA within a small (about 100 pL) and precisely located volume. The concentration in the target region increases at a constant rate, limited only by the amount of DNA injected into the capillary. With our experimental set up we were able to achieve amplification rates up to about 100 $s^{-1}$. The concentration in the trapped region increases at this rate until all of the injected DNA is located there.

Although diffusion tends to distribute molecules uniformly across a capillary, hydrodynamic flows, particularly when combined with an electric field, can produce strongly inhomogeneous distributions within a single cross-section. A flow field by itself produces a degree of focusing towards the center of the capillary, which hinders the detection of proteins [22] and DNA fragments by reducing the concentration at the walls of the capillary where the biomarkers are located. However, much stronger focusing can be obtained by combining a pressure driven flow with a uniform electric field [19, 21].

Figure 4:
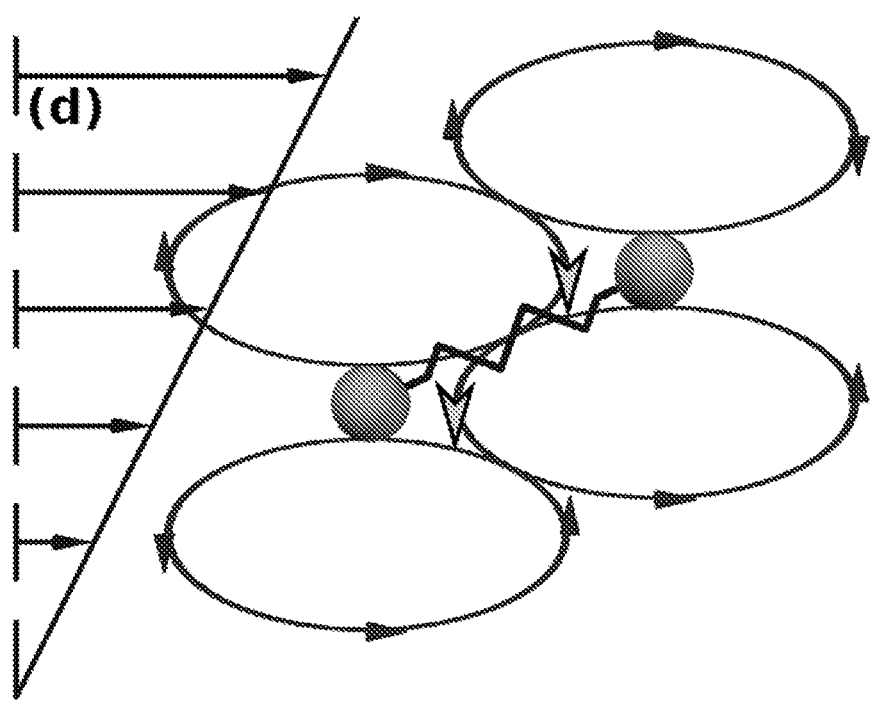
FIG. 4 shows a cartoon demonstrating the particle migration mechanism.

When the fluid flow and the electric field drive the particle in the same direction, the coupling between these fields causes a focusing of concentration at the center of the channel [19-21]. However, when the fields act in opposition the particle is driven towards the wall of the capillary [20]; the microfluidic channel used in the experiments reported here is sketched in FIG. 1. The mechanism by which migration may occur has been explained by a series of theoretical and numerical studies [23-25]. There is a coupling between the fluid flow and the electric field which causes a particle to migrate perpendicular to the field lines, as illustrated in FIG. 4. When the fields are opposed concentration at the wall is sharp; visual observations suggest all the DNA is located in a thin sheet of the order of 1 micron thick as illustrated by the sketch in FIG. 2. This is consistent with the diffusion coefficient of DNA (D on the order of $\mu m^2 s^{-1}$) and estimates of the migration velocity $v^\perp$ on the order of $m^2 s^{-1}$, which indicates a characteristic length scale for the concentration $D/v\perp<1$ μm. With a suitable combination of fluid flow and electric field, all of the DNA in a microcapillary can be driven to this thin boundary layer adjacent to the capillary walls. This is the first stage in focusing the DNA, and it rapidly (orders of seconds) increases the local concentration near the walls of the channel by more than an order of magnitude.

Figure 5:
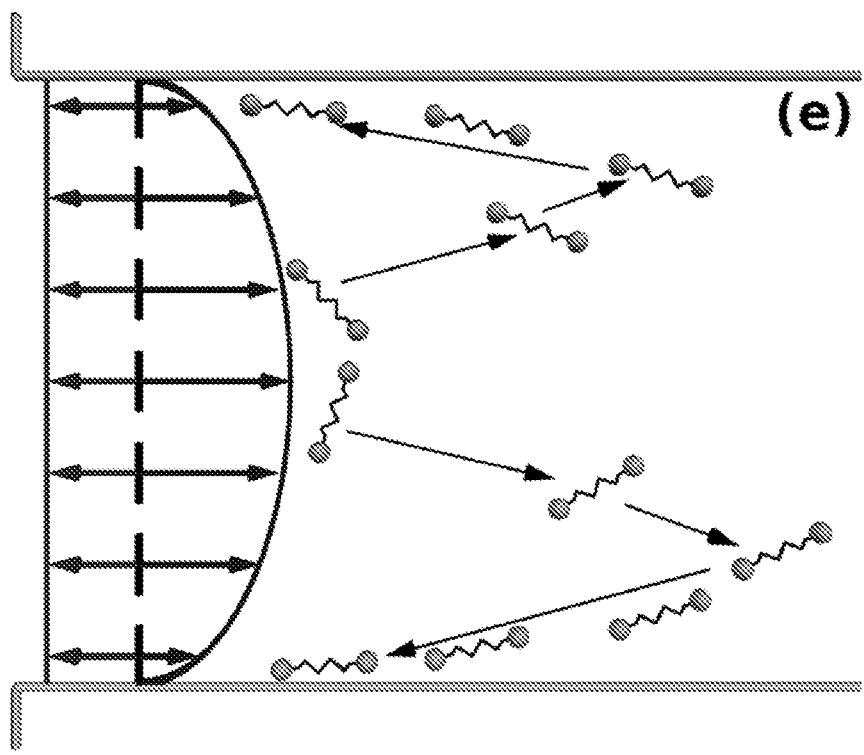
FIG. 5 shows a cartoon demonstrating the recirculation mechanism that results in an enhancement of the concentration of particle in the wall region of the channel of the microfluidic trap and the migration of the particle back towards the inlet of the microfluidic trap.

At the walls of the capillary the fluid velocity is small, and DNA is driven back towards the inlet by electrophoresis (FIG. 5). Thus DNA that flows into the capillary is returned to the inlet region by a recirculation mechanism combining migration and electrophoresis. However, for DNA to recirculate back to the inlet, it is essential that the walls of the device are coated with a neutral polymer to suppress electroosmosis.

In earlier work uncoated capillaries were used, which allows the DNA to escape the capillary because the electroosmostic flow is larger than the electrophoretic velocity. As shown by the images of the exit region in FIGS. 3A, 3C, and 3E (yellow), after the fields have been applied for 1 minute only an occasional DNA molecule escapes, despite the buildup of concentration at the inlet (purple). The distribution of DNA in the vertical (z) direction is localized into two thin sheets near the top and bottom walls, as indicated by the perspective sketch in FIG. 2. This is the second stage of amplification; the concentrated layer of DNA flows into a thin sheet at the inlet as shown in FIGS. 3A-3F Methods Silica microfluidic devices with a step change shown in FIG. 1 were designed in house and produced using a laser etching technique [26]. Given that the electrosmotic flow acts in the direction opposite to the electrophoretic motion for this material of construction for the channel, the concentration enhancement is most effective in the absence of any electrosmotic flow The effect of EOF can be reduced by coating the silica capillaries with a neutral polymer. Prior to every set of experiments, the microfluidic channels were cleaned with 1 M HCl for 5 hours, followed by rinsing with water for one hour, then cleaning with 1.25 M NaOH for 5 hours. Cleaned microfluidic channels were then coated with 1% PVP (polyvinylpyrrolidone) solution for overnight.

The DNA buffer solutions were prepared in 0.25× TE (Tris-EDTA) buffer solution with 1% (w/v) 2-Mercaptoethanol and 0.5% (w/v) PVP using YOYO-1 labeled T4 DNA (168 kbp) or λ DNA (48 kbp). The use of PVP in the buffer solution is to keep the active coating layer in the channel for repeatability. It was verified that excluding the PVP in the buffer solution does not affect the results for the first couple of hours.

Electric and flow fields were generated and are demonstrated in FIG. 1. Electrophoretic mobility of the DNA is measured to be 1.5 μm cm/Vs by tracking individual molecules in the absence of flow field. The average fluorescence intensity was determined by integrating over the viewing window.

Effect of the Electric Field and Flow

Figure 2:
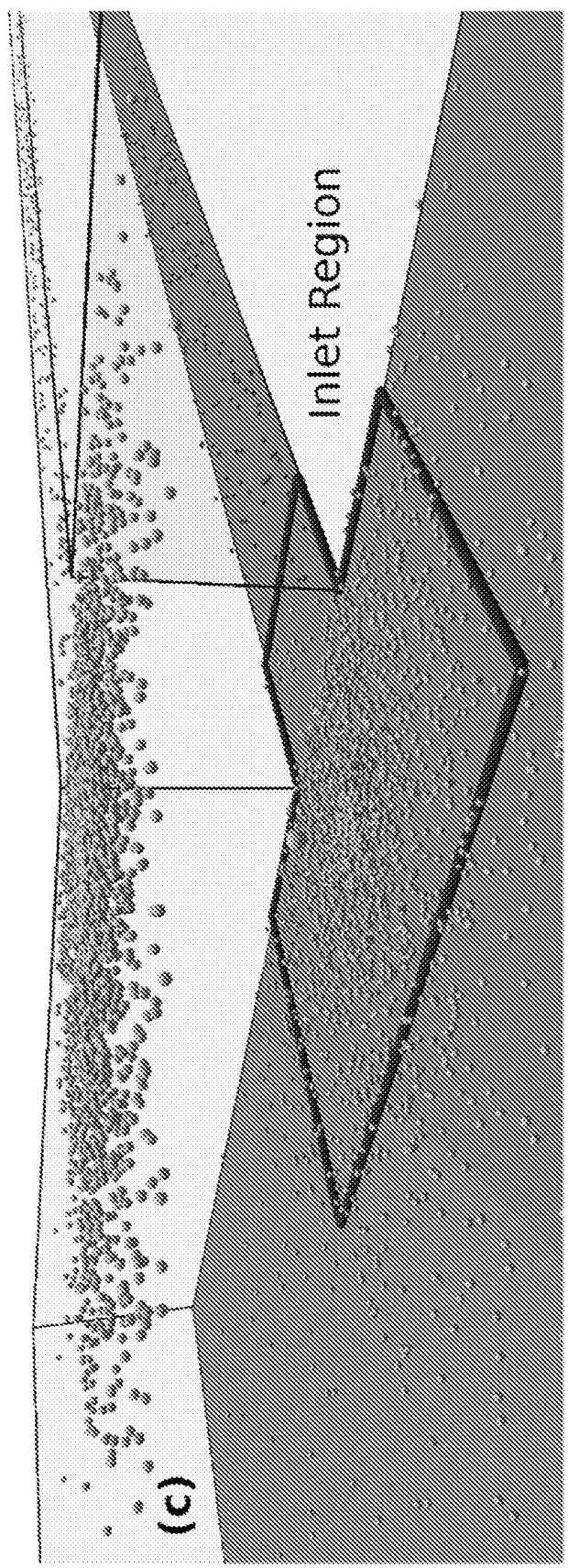
FIG. 2 shows a perspective view of one embodiment of an entry region of the microfluidic trap of FIG. 1.
Figure 3A:
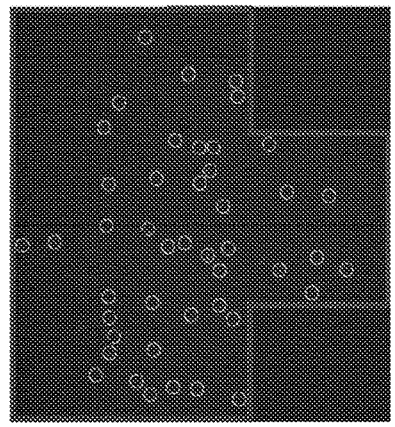
FIGS. 3A-3F show representative microscopic fluorescence images (40×) at a channel inlet (FIGS. 3A, 3C, 3E) and a channel outlet (FIGS. 3B 3D, 3F). The microscope was focused on a plane about 5 µm from the wall of the channel. The DNA velocity in this plane in the thin portion of the channel was about 50 µm/s. The fluid velocity, in the thin portion of the channel was about 1200 µm/s as evaluated at the centerline of the thin portion of the channel.
Figure 3B:
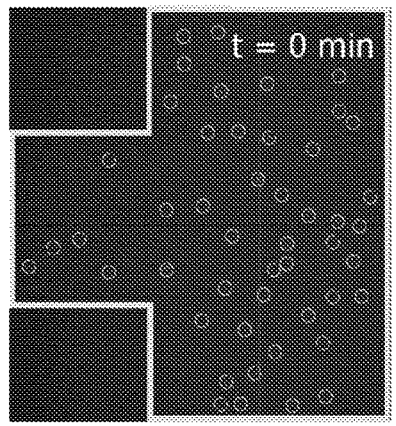
Figure 3C:
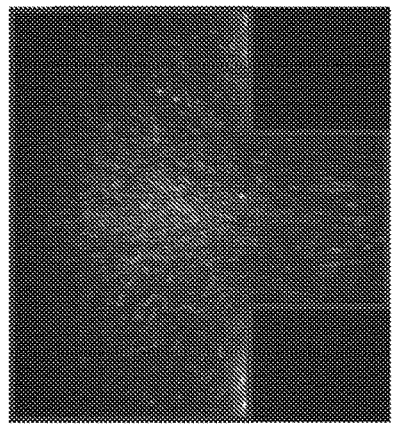
Figure 3D:
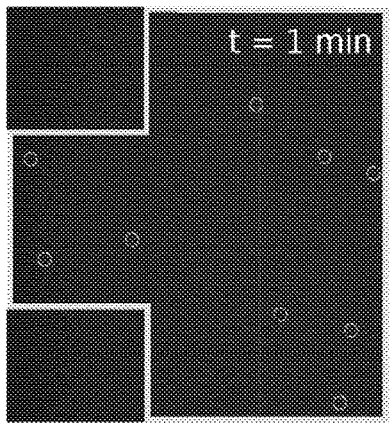
Figure 3E:
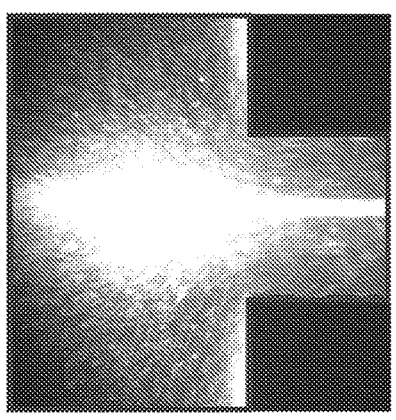
Figure 3F:
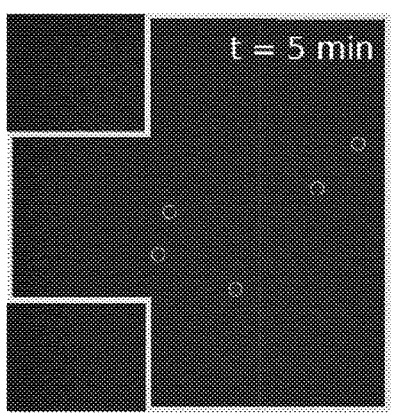
Figure 6A:
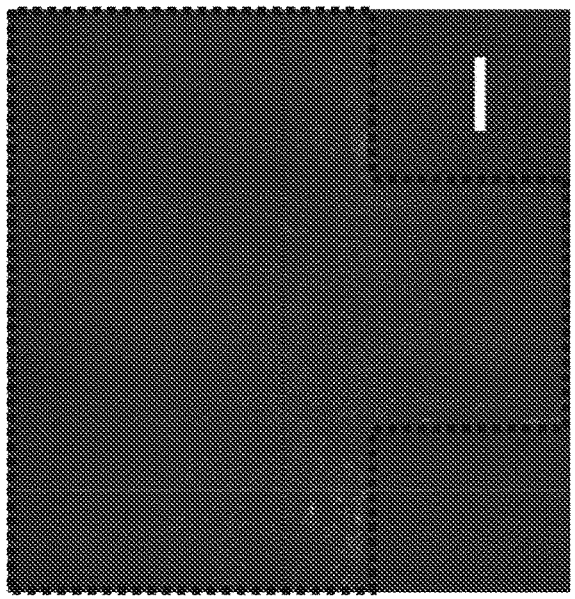
FIGS. 6A-6D shows representative microscopic fluorescence images that demonstrate the effect of an electric field on a particle. The flow rate was 1200 µm/s and the electrophoretic velocities of the particle in the thin portion of the microchannel was about 16.7 µm/s (FIG. 6A), 33.3 µm/s (FIG. 6B), 50 µm/s (FIG. 6C), 100 µm/s (FIG. 6D).
Figure 6B:
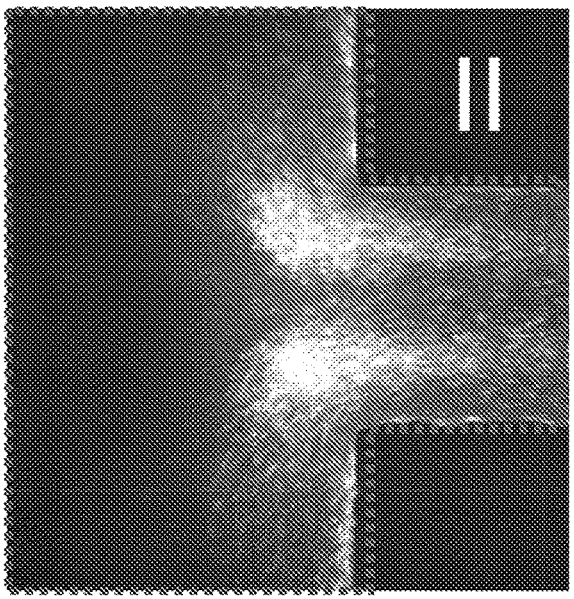
Figure 6C:
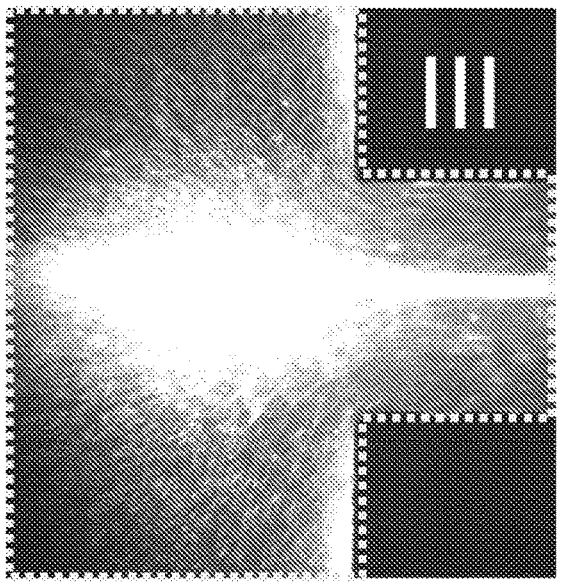
Figure 6D:
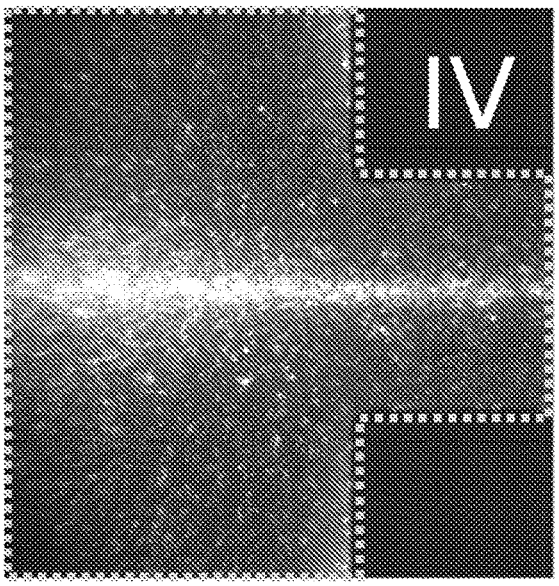
Figure 7:
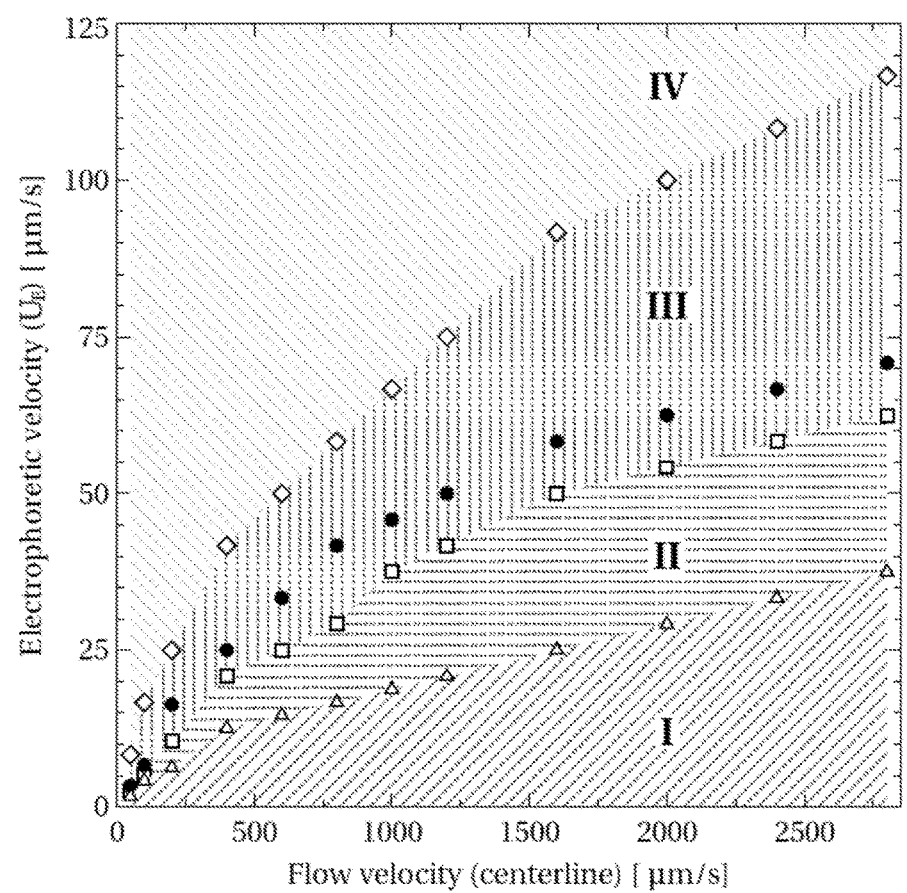
FIG. 7 shows a graph demonstrating the phase diagram of the different trapping regions demonstrated in FIGS. 6A-6B.

DNA migrates to the walls of the capillaries over a wide range of flow rates and electric fields; however it can become trapped in the inlet region as illustrated in FIGS. 3A-3F for a narrow band of flow rates and electric fields. The final image in FIGS. 3E and F (after 5 minutes) corresponds to region III in FIGS. 6C and 7. At higher electric fields (IV) the DNA was observed to be drawn further back into the inlet region by the enhanced electrophoresis, reducing the amount of DNA in the trapped region, whereas at lower electric fields (regions I and II) the DNA was observed to start to escape. As the concentration in the trap decreases (because of the reduced electric field) the single concentrated region first splits into two much weaker bands (II) and then disappears entirely (I). It is important to keep in mind that the concentration field is three dimensional. The intensity in the images is being generated from thin sheets of DNA close to the top and bottom walls of the device (FIG. 2). A quasi phase diagram is shown in FIG. 7, indicating the four different regions of trapping at each flow rate. The field that produces the most compact region of trapped DNA at each flow rate is identified by the solid circles. In the remainder of the work electric field is adjusted to stay on the curve indicated by the solid circles and thereby maximize the trapping.

Rate Measurements

Application of the electric and flow increases the DNA concentration in the entry region. Quantitative estimation of the DNA trapped in the region is important to reveal the underlying mechanism of the system. It is not possible to count individual molecules at the concentrations reached in the trap, even if the incoming solution is very dilute (<10fM). Instead, the growth of fluorescence intensity of the trapped DNA as a marker for the increase in concentration is monitored. Since DNA accumulates without limit (at least over times up to 1 hour), the most important factor is the concentration amplification rate ($A=c_0^{-1} dc/dt$) where $c_0$ is the concentration of the solution. This indicates the maximum practically achievable amplification with the present experiment. Later it is showed amplifications factors of over $10^4$ can be achieved in less than 30 minutes. Quantification of the DNA in the trap can be achieved by measuring the light emitted from the labeled DNA. However, quantitative inferences from the measured fluorescence intensity introduce several complications. First, the fluorescing molecules are rapidly bleached by the light source. Second, as the concentration in the trap builds up, the intensity rapidly exceeds the dynamic range of the camera. Instead, the rate of recovery of fluorescence intensity after bleaching is measured, which corresponds to the new DNA that is entering the trap.

Figure 8:
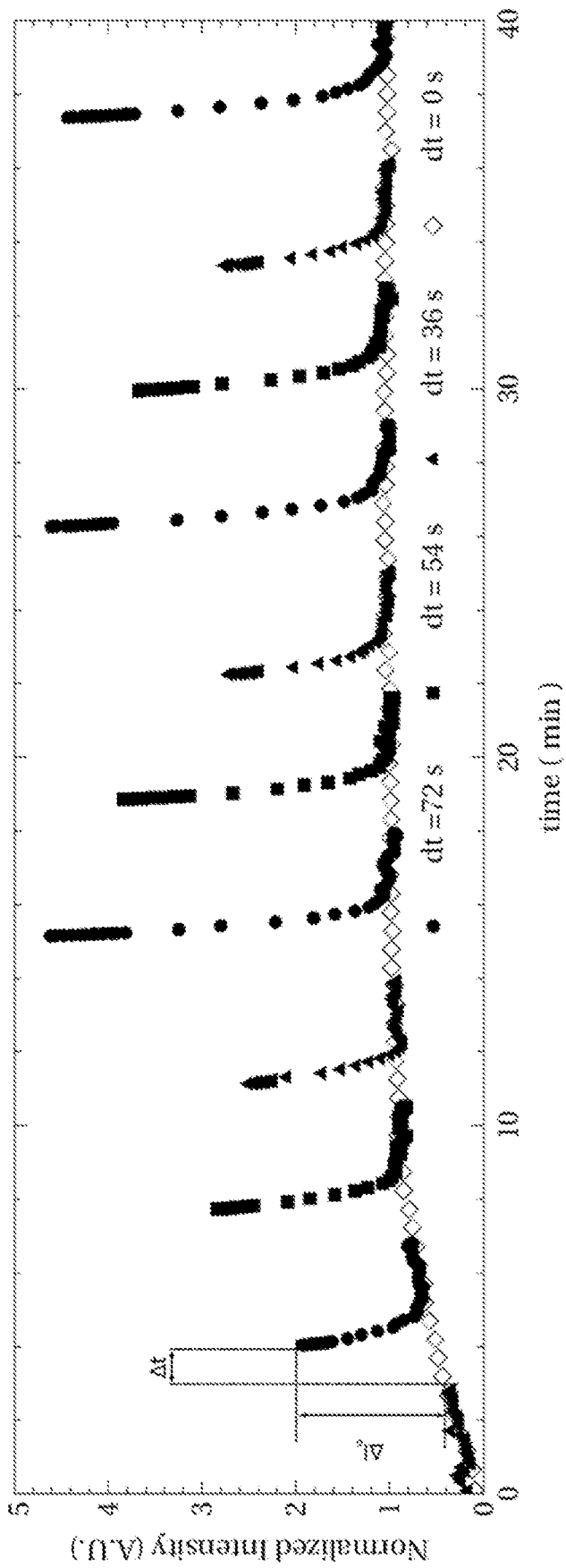
FIG. 8 shows a graph demonstrating the results from concentrating T4 DNA in a microfluidic trap as substantially described herein at a centerline velocity of about 1200 μm/s and an electrophoretic velocity of about 50 μm/s. Data points (solid symbols) were recorded by illuminating the sample; the shutter remained closed for between 36 (triangles), 54 (squares) and, 72 (circles) seconds. The open diamonds shown the data points obtained when the sample was illuminated with a constant light exposure.

A sample set of results from these experiments is shown in FIG. 8. The computer controlled shutter was used to illuminate the sample for predetermined periods of time. Once the sample is illuminated, the intensity (solid symbols) decreases due to photobleaching, finally reaching an asymptotic value $I_\infty$ when the influx of new unbleached DNA into the trap balances the loss of intensity due to the bleaching. Once the shutter is turned off photobleaching stops, while the flux of fresh DNA into the trap continues. The difference between the peak intensity $I_{max}$ and $I_\infty$ can be used to determine the rate at which new DNA flows into the trap:

$$\frac{dC}{dt} = \beta \frac{I_{max} - I_\infty}{\Delta t} = \beta \frac{dI}{dt}, \quad \text{Equation 1}$$

where $\Delta t$ is the time the shutter remained closed. An experiment with constant illumination (open diamonds) shows the asymptotic value which is independent from $I_{max}$. Experiments carried out with different $\Delta t$ show that the increase in concentration is proportional to $\Delta t$. The coefficient $\beta$ is determined from calibration experiments, by measuring the fluorescence intensity of solutions with known concentration.

Figure 9:
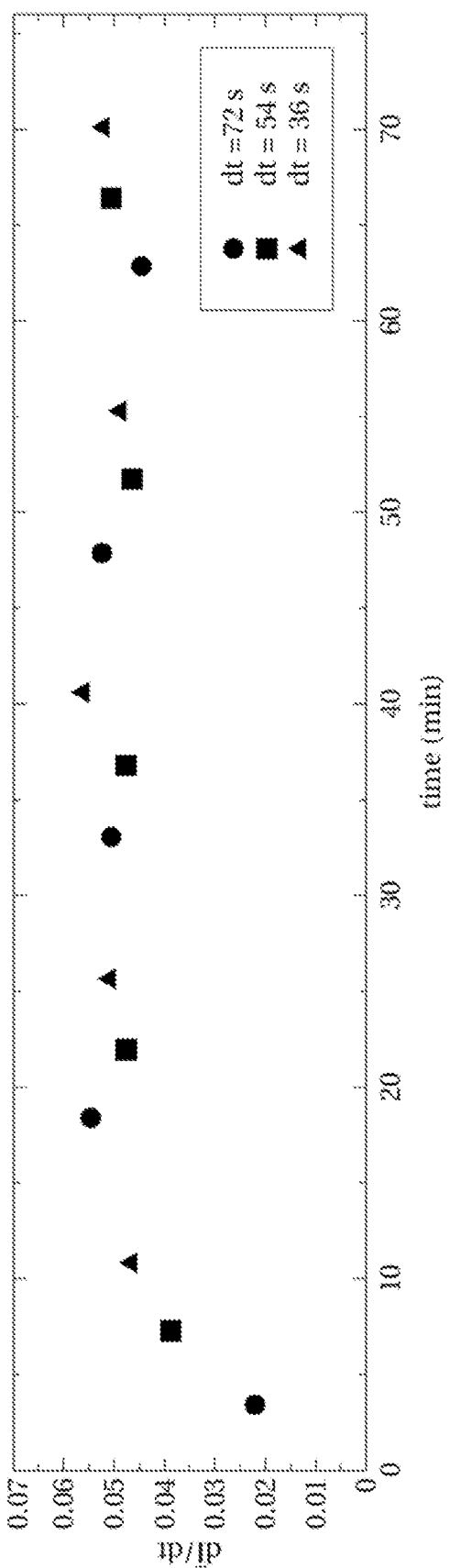
FIG. 9 shows a graph demonstrating the amplification rate of the intensity at three shutter rates.
Figure 10:
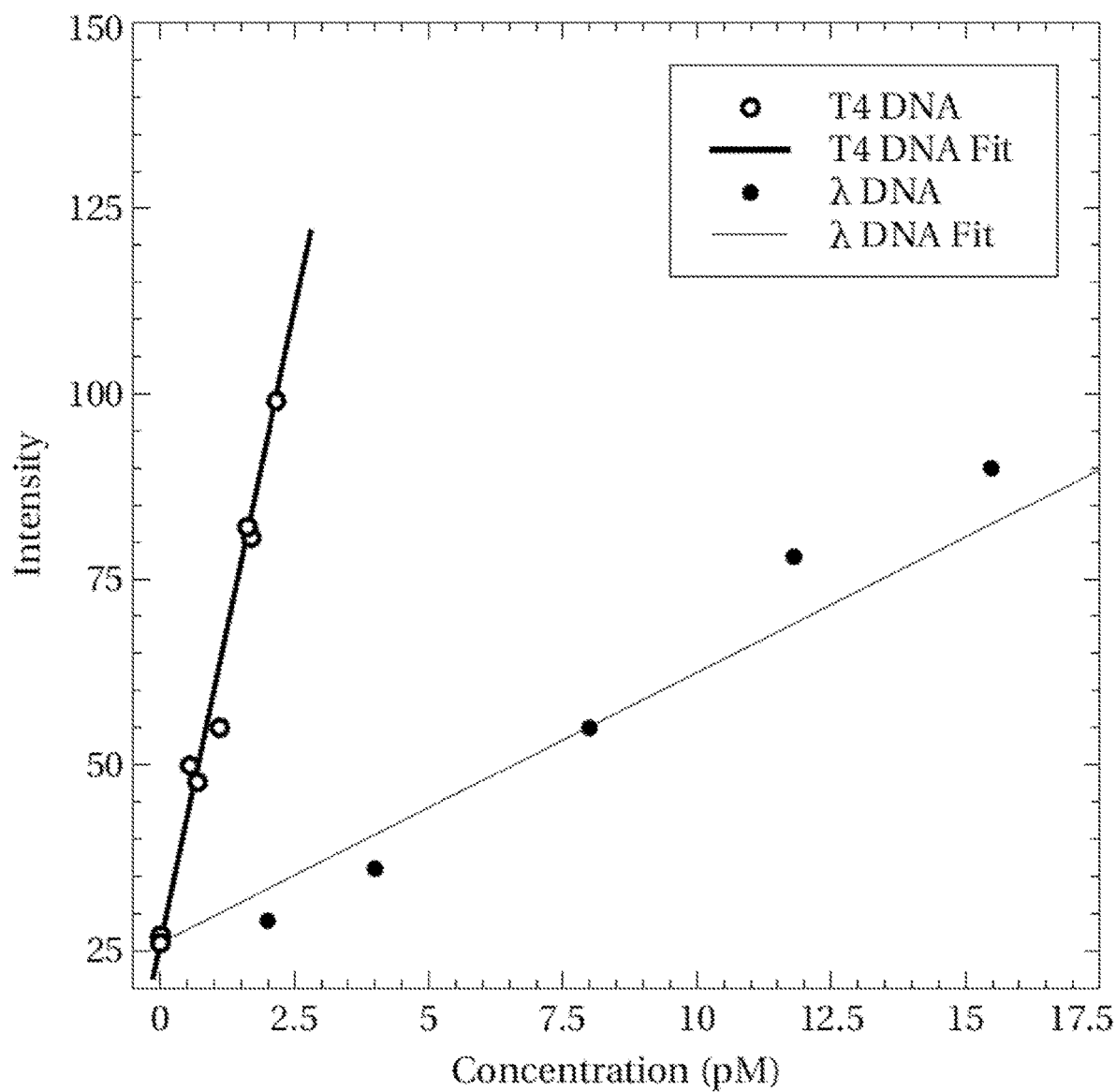
FIG. 10 shows a graph demonstrating the intensity of T4 and λ DNA at different concentrations, which are shown using open (T4) and closed (λ) circle. A linear least square fit method was used (solid lines) to obtain the slope of the DNA concentration. The linear calibration ($\beta(I-I_0)=C$) results to $\beta_{T4}=0.03$, $\beta_\lambda=0.3$ and $I_0 26$.

The rate (dI/dt) as a function of experimental time for the values shown in FIG. 8 is plotted in FIG. 9. Over the first few shutter openings the rate increases monotonically, but eventually it reaches an asymptotic value, implying a constant rate of concentration amplification over the remainder of the experiment. The rate of the intensity can be converted to a concentration if the corresponding intensity at that concentration is known in other words the β value defined in Eq. 1 is known. Intensity of DNA solutions at known concentrations were measured and the calibration results are shown in FIG. 10. The β values measured from the calibration experiments are $\beta_{T4}=0.03$ and $\beta_\lambda=0.3$.

Figure 11:
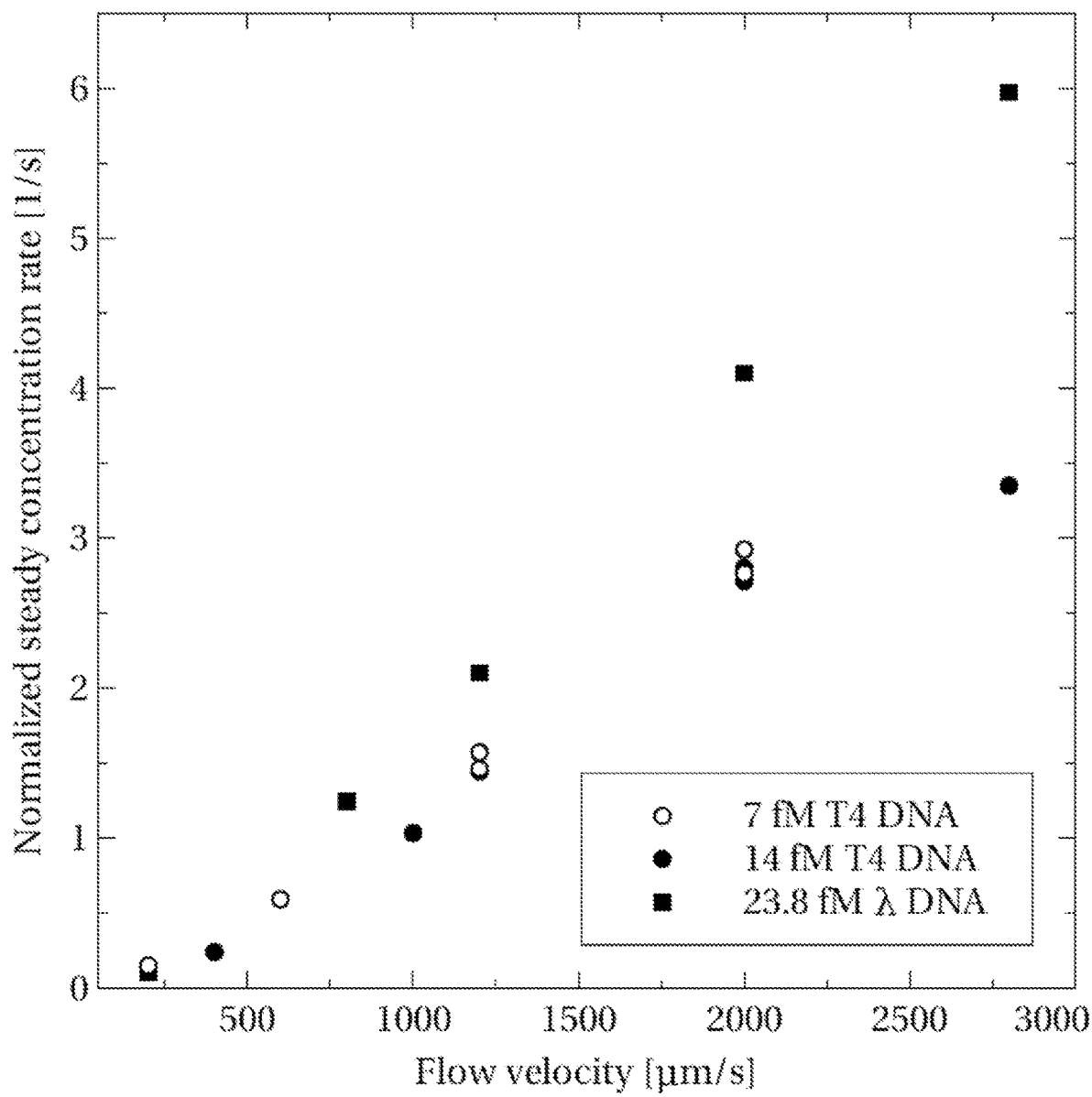
FIG. 11 shows a graph demonstrating the normalized steady state concentration rate for the microfluidic trap when the trap area is assumed to extend across the depth of the device. The rates were calculated using two different DNA types at three different concentrations. The 7 fM and 14fM T4 DNA solutions resulted in the same values within the error range. This demonstrates that the normalized rate is independent of the DNA concentration. The λ DNA concentration rates are shown in solid square symbols.

The asymptotic rates of concentration amplification for different DNA samples are shown in FIG. 11 as a function of the flow rate. Increasing the flow velocity resulted in an increase in the concentration rate. The T4 data shows that initial concentration does not affect the normalized rate (open and solid circles). At high flow rates λ DNA has higher rates compared to T4 DNA.

Concentration Layer Distance from the Wall

Figure 12:
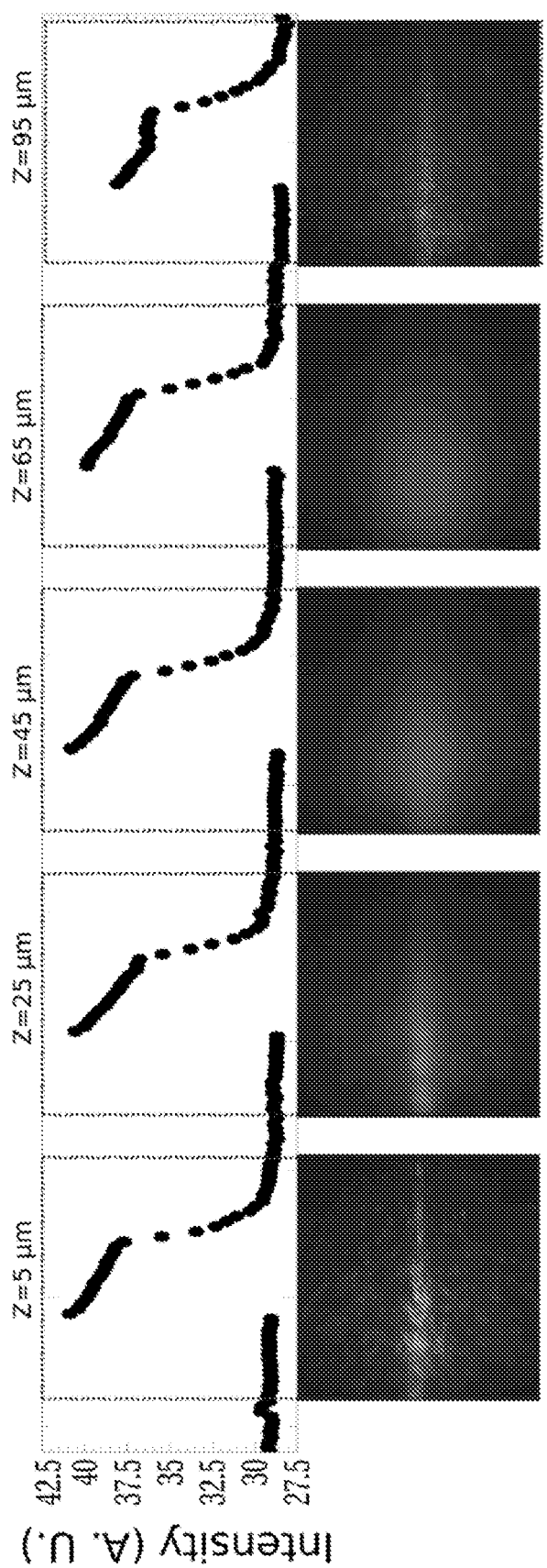
FIG. 12 shows graphs and corresponding fluorescent microscopic images demonstrating the intensity at the channel inlet of the microfluidic trap at five different imaging depths at a centerline velocity of 1200 μm/s and an electrophoretic velocity of about 50 μm/s.

The concentration rates shown in FIG. 11 assume that the DNA is distributed homogeneously across the channel. As it was sketched in FIG. 1 the DNA is concentrated close to the wall. Experimentally this can be observed by scanning the channel at different depths, which is shown in FIG. 12. The DNA can only be seen in two layers in the channel. The light emitted from the DNA however, is not bounded in the trap region and can be observed at every depth in the channel. The experimental methods can only determine the thickness of the layer with 5 micron accuracy.

A more accurate way to determine the concentration layer is by balancing the flow and electrophoretic velocities. The flow velocity is zero at the wall and increases to a maximum value in the center. The electrophoretic velocity of the DNA is uniform across the channel. The point where there two velocities match gives the distance of concentration layer from the wall. Only the DNA molecules below this region can recirculate to the inlet. The stagnation point at the center of the channel wall is estimated in FIG. 7 and shown in open square symbols. This point shows how far the concentration layer is from the center of the wall. The calculated layer thicknesses from the wall with respect to the flow velocity are shown in FIG. 13.

Figure 13:
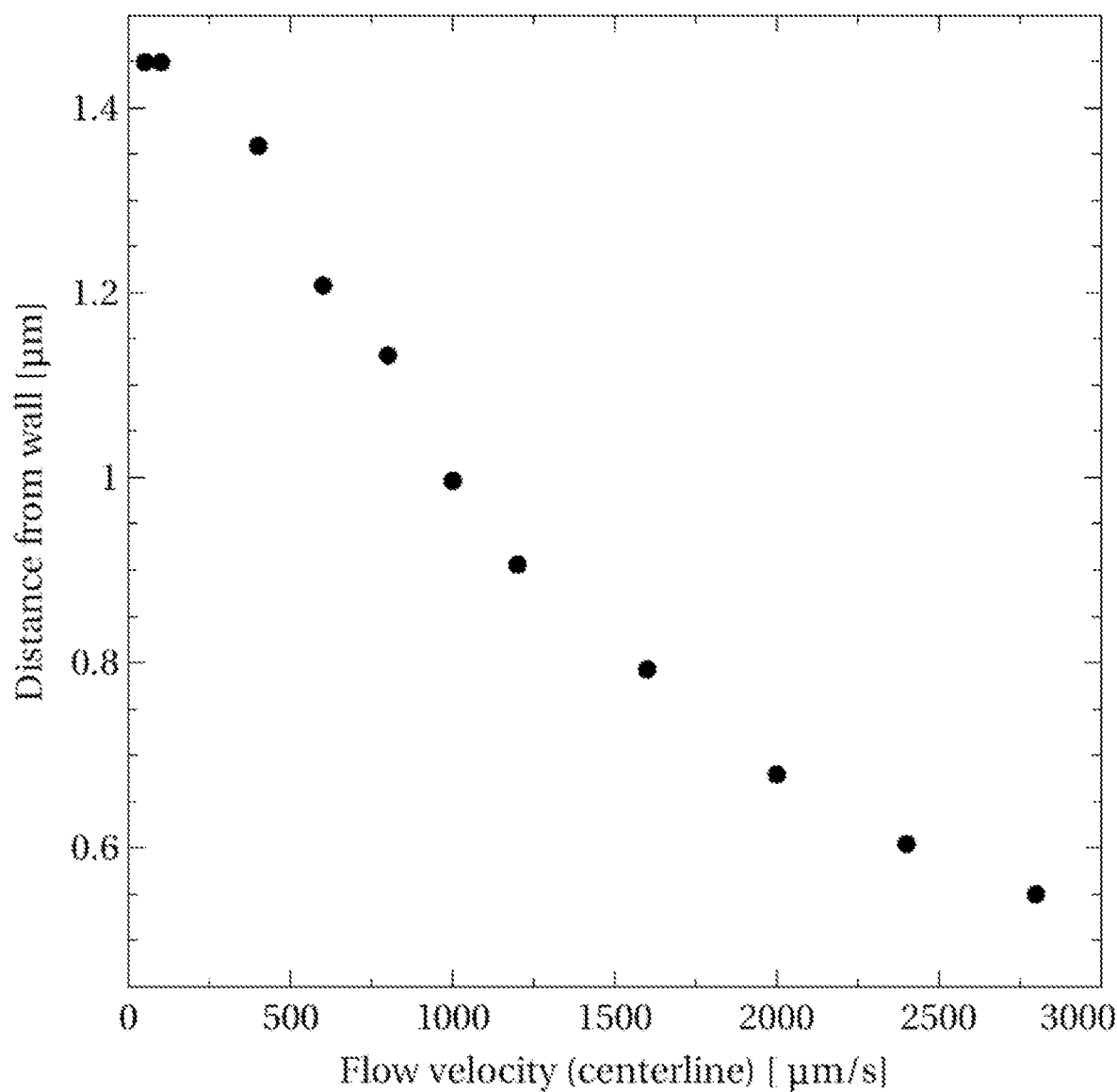
FIG. 13 shows a graph demonstrating the estimated distance from the wall at which the flow field balances the electrophoretic velocity. The DNA, upon entering the channel, migrates to within this distance of the wall in order to be trapped. The distance was calculated with the conditions presented in FIG. 7 circles by balancing the electrophoretic velocity to the centerline flow velocity at the corresponding height.
Figure 14:
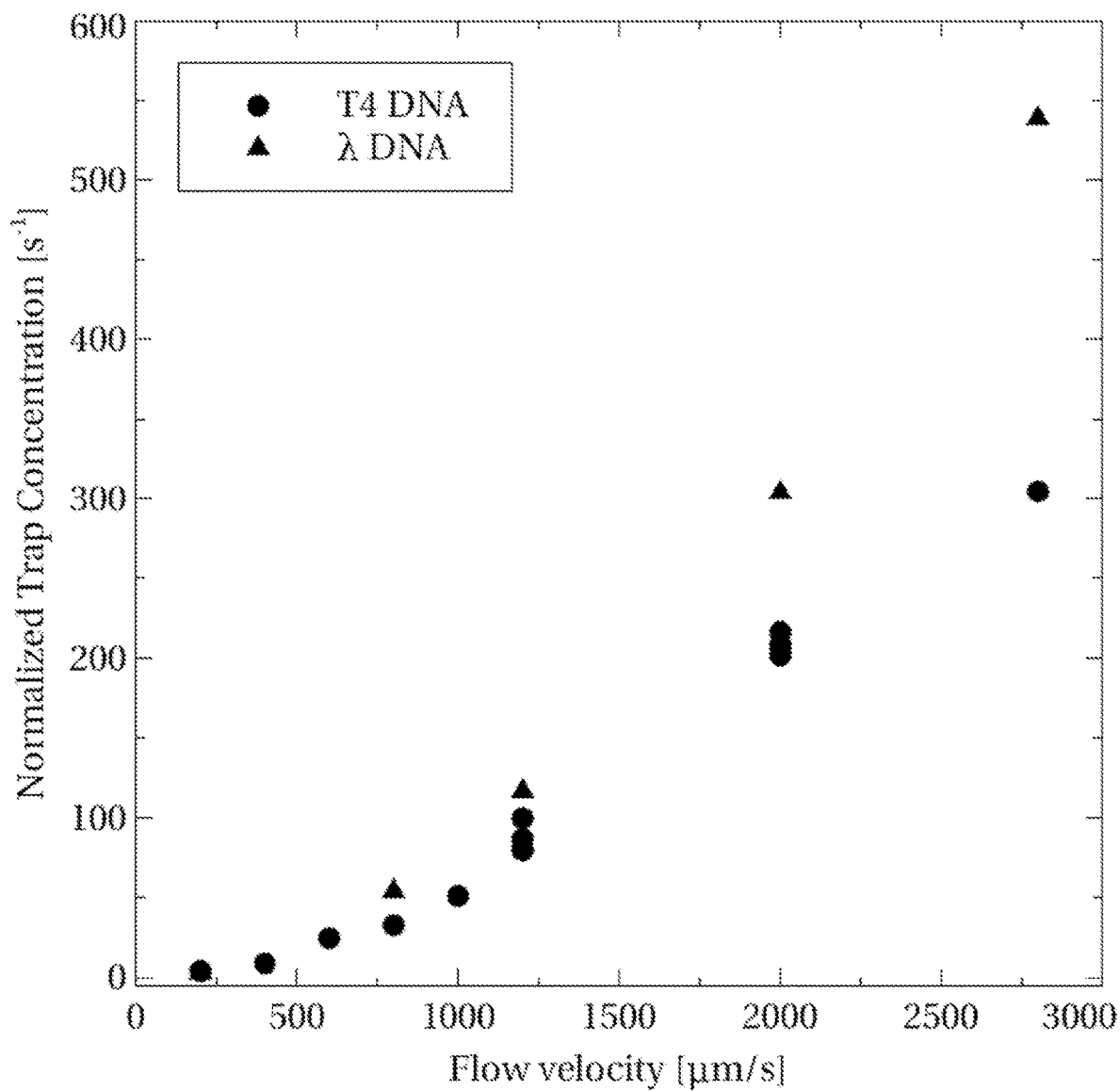
FIG. 14 shows a graph demonstrating the normalized trap concentration rate as a function of flow velocity. Here, the heights from FIG. 13 were used for the estimate of the trap volume, as opposed to the results in FIG. 11 where the total height of the device was used in the estimate.

The localized trap concentration is calculated by using the normalized steady concentration rate shown in FIG. 11 with the trap thickness shown in FIG. 13. The normalized trap concentration shown in FIG. 11 assumes that the DNA is distributed across the channel. The vertical scanning experiment in FIG. 12 shows that the DNA is localized only in two sections and further calculations shown in FIG. 13 identifies the trap thickness. The corrected localized concentration is calculated in FIG. 14 by first separating the contributions from top and bottom trap then correcting the trap volume for the corresponding concentration.

Microfluidic Gate Model

Figure 15:
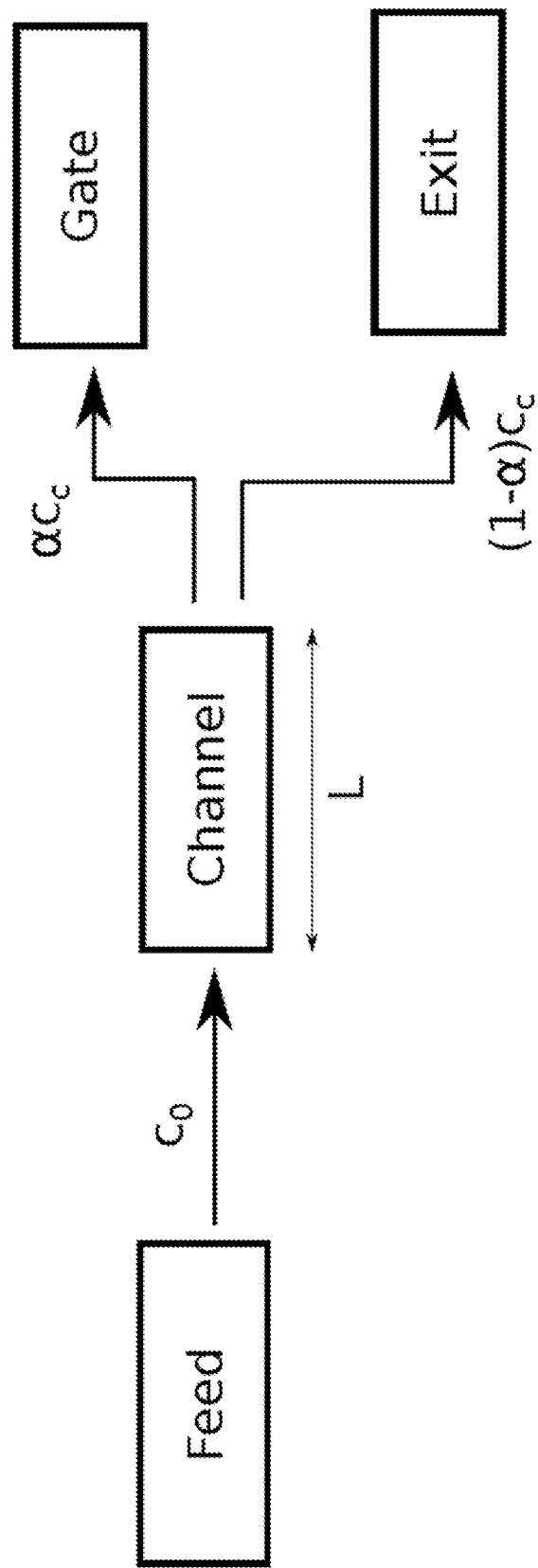
FIG. 15 shows a cartoon demonstrating a macroscopic conceptual model of particle concentration/trapping in the microfluidic trap as substantially described herein. Fluid from the reservoir can be fed to the channel of the microfluidic trap with a concentration $c_0$. The channel can feed the DNA solution to the trap at a concentration of $c_c$ with an efficiency of α.

The microfluidic gate can be modeled in two steps. A simple schematic of the gate model is illustrated in FIG. 15. Initially, the concentration of DNA in the microchannel is (on average) the bulk concentration c0 while the flux of DNA into the channel is $U_{avg}h^2c_0$, where h is the channel thickness (h=100 μm). The bulk solution is fed to the channel with a cross-sectional area of h2 and distributed across the channel length L. Average flow velocity ($U_{avg}$) in the channel can be calculated by dividing the center velocity ($U_c$) by 2.1, which was calculated by integrating the flow profile solution for a square channel. A portion of the DNA ($\alpha c_c$) in the channel with concentration of $C_c$ lends on the gate and the rest, $(1-\alpha)c_c$, leaves the channel through the exit. The constant α is similar to an efficiency constant showing how effective the DNA can recirculate back to the gate. The rate equation for the channel concentration becomes, $$L\frac{dC_c}{dt} = c_0 U_{avg} - \alpha U_E C_c - (1-\alpha)C_c(U_{avg} - U_E). \quad \text{Equation 2}$$

The concentration in the gate is then, $$\frac{dc_g}{dt} = \frac{\alpha U_E C_c h^2}{2V_g}, \quad \text{Equation 3}$$

where Vg is the volume of the trap and cg is the concentration at the gate. The Vg value is determined by using the distance from the wall defined in FIG. 13 with the image region. The asymptotic values calculated from the model at the experimental conditions can be compared with the experimental results.

Results

Figure 16:
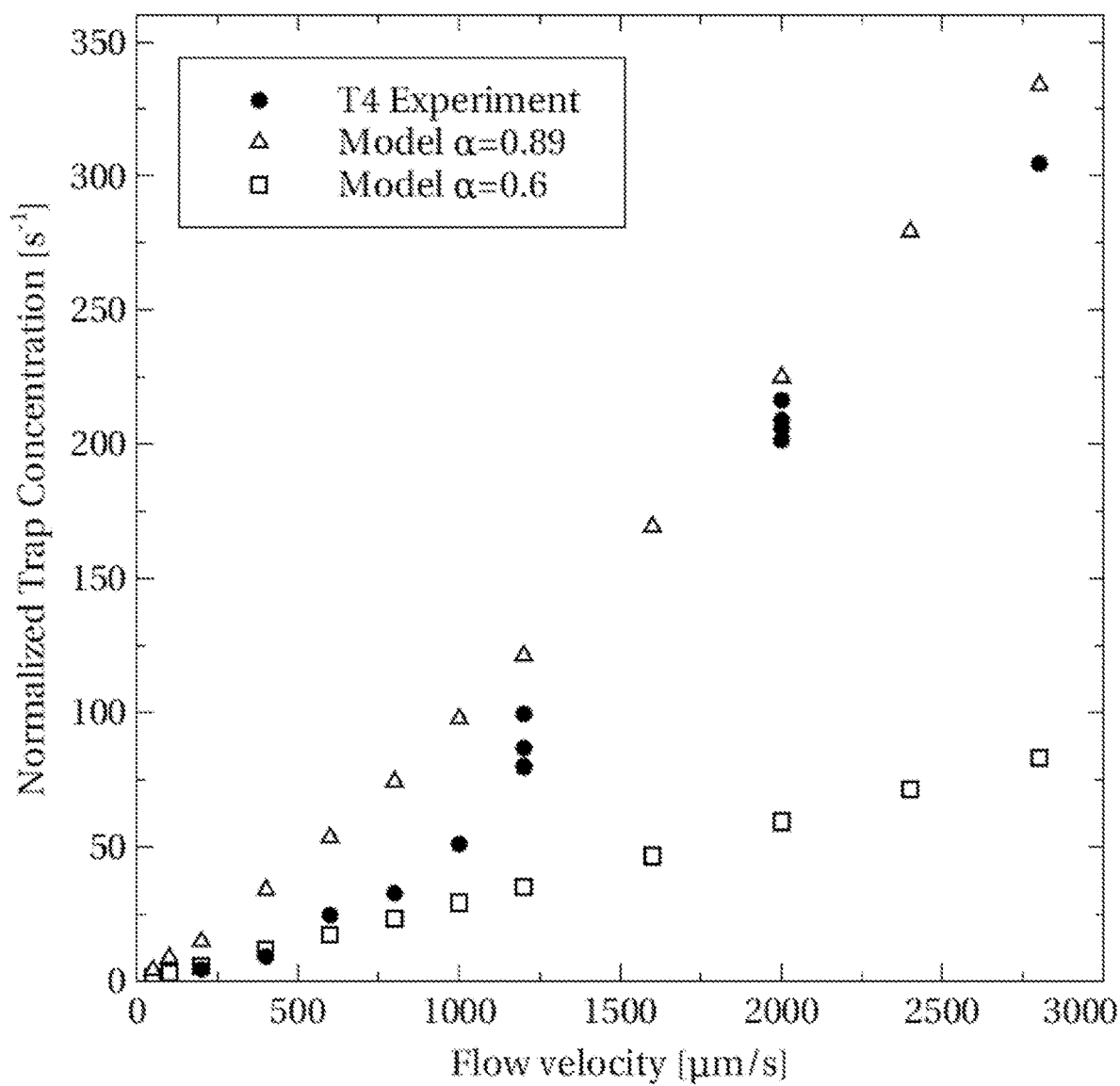
FIG. 16 shows a graph demonstrating the normalized trap concentration for T4 DNA with two different efficiency constants α.

Gate concentration estimated from the model with two different efficiency constants α is plotted with the experimental results, as a function of flow velocity in FIG. 16. The normalized trap concentration is bounded between α=0.6 and α=0.89. The higher velocities show a higher efficiency meaning the concentration profile is sharper at higher velocities. This observation is consistent with the kinetic model where higher fields result in a sharper concentration profiles closer to the walls [25].

Figure 17:
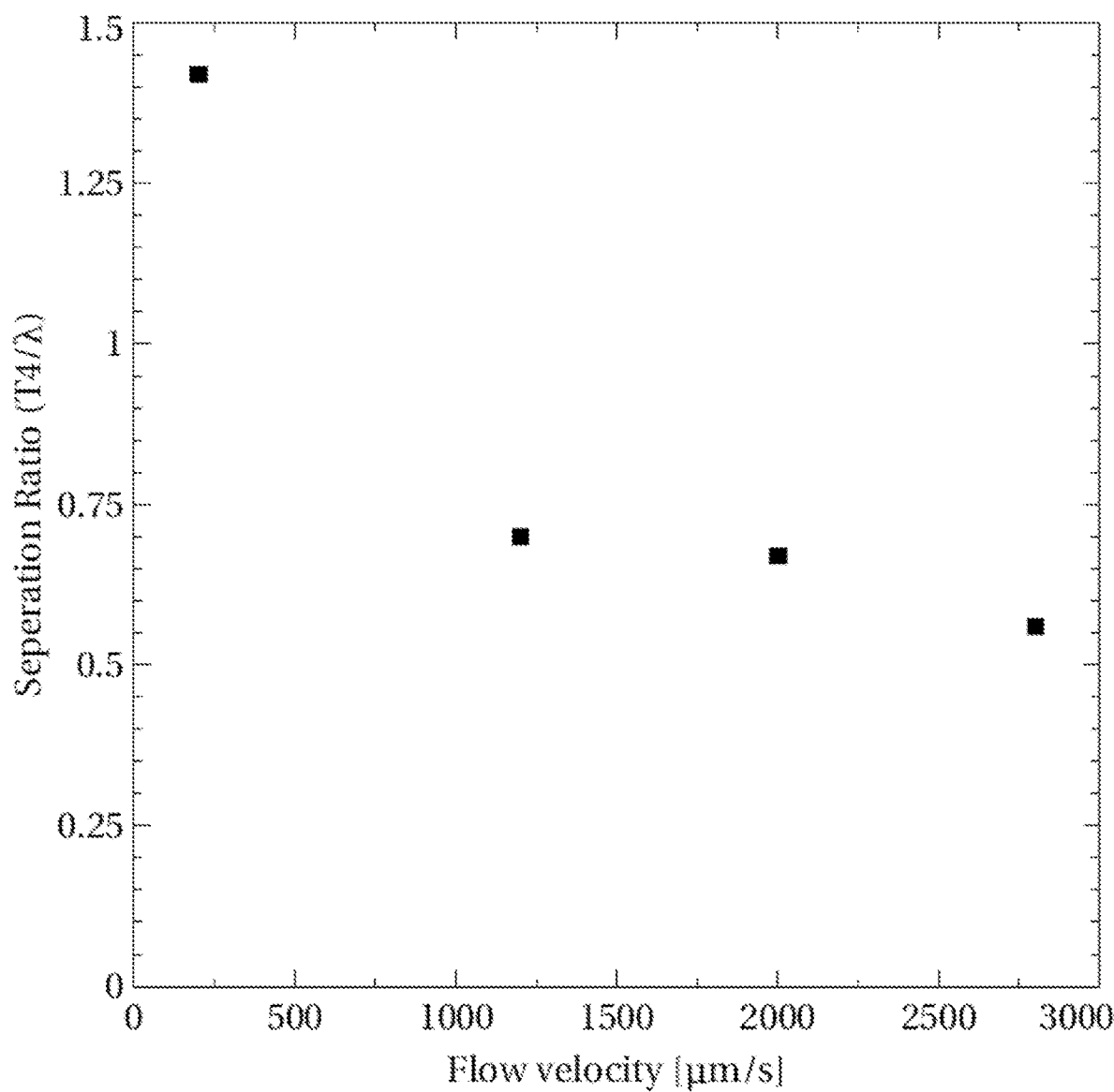
FIG. 17 shows a graph demonstrating the separation ratio for T4 DNA and λ DNA. The separation ratio below 500 μm flow velocities show that the gate traps T4 DNA more effectively than the λ DNA.

The ratio of the trap concentration rates for T4 and λ DNA at same flow and electric field is shown in FIG. 17. The difference in the concentration rates can be used to separate and concentrate DNA at different length. Flow velocities around 200 μm/s has a ratio of 1.5 meaning T4 DNA can be concentrated 1.5 times faster than λ.

Summary

The microfluidic device used in these experiments increased the average DNA concentration in the inlet region of the microfluidic device about 20,000 fold at the highest flow rate. This is the average concentration over the whole inlet region (shown in purple in FIGS. 3A, 3C, and 3E). However, because the DNA in trapped in a thin layer (about 1 μm thick) near the top and bottom surfaces of the device (FIG. 2) the actual concentration in these layers is amplified by close to 106 in the same time. This discovery suggests that the sensitivity of devices used to detect small concentrations of DNA and other biopolymers could be enhanced by many orders of magnitude by the simple expedient of applying an appropriate flow rate and electric field. The performance of detectors relying on flow to introduce the polymers is hindered by hydrodynamic lift, which decreases the concentration near the walls, where the detectors are placed. However with the addition of an opposing electric field a very large concentration can be achieved at the detector. A further feature of the system is that the location of the region of maximum concentration is very reproducible.

REFERENCES

[1] C.-C. Lin, J.-L. Hsu and G.-B. Lee, *Microfluidics and Nanofluidics*, 2011, 10, 481-511.
[2] J. Han and H. G. Craighead, *Science*, 2000, 288, 1026-1029.
[3] J. M. Martel, K. C. Smith, M. Dlamini, K. Pletcher, J. Yang, M. Karabacak, D. A. Haber, R. Kapur and M. Toner, *Scientific reports*, 2015, 5, 1-5.
[4] V. Ugaz and J. Christensen, *Microfluidic Technologies for Miniaturized Analysis Systems*, Springer US, 2007, pp. 393-438.
[5] T. Shendruk, O. Hickey, G. Slater and J. Harden, *Curr. Op. Coll. Inter. Sci.*, 2012, 17, 74-82.
[6] J.-L. Viovy, *Rev. Mod. Phys.*, 2000, 72, 813-872.
[7] T. T. Perkins, D. E. Smith and S. Chu, *Science*, 1997, 276, 2016-2021.
[8] D. E. Smith and S. Chu, *Science*, 1998, 281, 1335-1340.
[9] E. S. Shaqfeh, *J. Non-Newton. Fluid*, 2005, 130, 1-28.
[10] Y.-L. Chen, H. Ma, M. D. Graham and J. J. de Pablo, *Macromolecules*, 2007, 40, 5978-5984.
[11] R. M. Jendrejack, M. D. Graham and J. dePablo, *J. Chem. Phys*, 2003, 119, 1165-1173.
[12] R. M. Jendrejack, E. T. Dimalanta, D. C. Schwartz, M. D. Graham and J. J. de Pablo, *Phys. Rev. Lett.*, 2003, 91, 038102.
[13] R. M. Jendrejack, D. C. Schwartz, J. J. de Pablo and M. D. Graham, *The Journal of Chemical Physics*, 2004, 120, 2513-2529.
[14] H. Ma and M. D. Graham, *Phys. Fluids.*, 2005, 17, 083103.
[15] H. Stone, A. Stroock and A. Ajdari, *Annu Rev Fluid Mech*, 2004, 36, 381-411.
[16] A. D. Stroock, S. K. Dertinger, A. Ajdari, I. Mezi´c, H. A. Stone and G. M. Whitesides, *Science*, 2002, 295, 647-651.
[17] R. H. Liu, M. Stremler, K. V. Sharp, M. G. Olsen, J. G. Santiago, R. J. Adrian, H. Aref, D. J. Beebe et al., *Microelectromechanical Systems, Journal of,* 2000, 9, 190-197.
[18] N.-T. Nguyen and Z. Wu, *Journal of Micromechanics and Microengineering*, 2005, 15, R1.
[19] J. Zheng and E. S. Yeung, *Anal. Chem.*, 2002, 74, 4536-4547.
[20] J. Zheng and E. S. Yeung, *Anal. Chem.*, 2003, 75, 3675-3680.

[21] M. Arca, J. E. Butler and A. J. C. Ladd, *Soft Matter*, 2015, 11, 4375-4382.
[22] Y.-C. Wang, A. L. Stevens and J. Han, *Analytical Chemistry*, 2005, 77, 4293-4299.
[23] O. B. Usta, J. E. Butler and A. J. C. Ladd, *Phys. Rev. Lett.*, 2007, 98, 098301.
[24] R. Kekre, J. E. Butler and A. J. C. Ladd, *Phys. Rev. E*, 2010, 82, 050803.
[25] J. E. Butler, O. B. Usta, R. Kekre and A. J. C. Ladd, *Phys. Fluids*, 2007, 19, 113101.
[26] K. H. Leong, *Industrial Laser Solutions*, 2004, 19, 1-5.

We claim:

1. A microfluidic device consisting of:
   an inlet area, where the inlet area has an entry region;
   an outlet area, where the outlet area has an exit region;
   a single microcapillary, where the microcapillary is fluidly coupled to the entry region of the inlet area and the exit region of the outlet area, and wherein the microcapillary is coated with a charge-neutral compound or charge-neutral polymer, wherein the inlet area, the outlet area, and the single microcapillary are formed from a single structure using laser etching;
   a fluid flow generator configured to generate a fluid flow through the microcapillary;
   an electric current generator configured to generate an electrophoretic flow through the microcapillary, where the electrophoretic flow is in opposition to the fluid flow, and where the electrophoretic flow is tuned to the fluid flow such that one or more types of particles present in the microcapillary migrate to a wall of the microcapillary and subsequently migrate against the fluid flow to a stagnation region,
   and wherein the microfluidic device has one or more step-changes in cross-sectional area in one or more areas across a length of the device.

2. The microfluidic device of claim 1, wherein the width of the microcapillary ranges from about 0.1 µm to about 2 mm.

3. The microfluidic device of claim 1, wherein the length of the microcapillary ranges from about 100 µm to about 1 m.

4. The microfluidic device of claim 1, wherein the inlet area has a height ranging from about 0.1 µm to about 500 µm and a length ranging from about 0.1 µm to about 1 m.

5. The microfluidic device of claim 1, where the electric current generator is further configured to apply an axial electric field to the fluid.

6. The microfluidic device of claim 1, wherein the fluid flow generator is configured to generate a fluid flow through the microcapillary at a flow velocity of 0 µm/s to 3000 µm/s.

7. A microfluidic device consisting of:
   an inlet area, where the inlet area has an entry region;
   an outlet area, where the outlet area has an exit region;
   a single microcapillary, where the microcapillary is fluidly coupled to the entry region of the inlet area and the exit region of the outlet area, and wherein the microcapillary is coated with a charge-neutral compound or charge-neutral polymer, wherein the inlet area, the outlet area, and the single microcapillary are formed from a single structure using laser etching;
   a fluid flow generator configured to generate a fluid flow through the microcapillary;
   a reservoir, wherein the reservoir is fluidly coupled to the microcapillary, and wherein a capture molecule is coupled to or is physically attached to a region of the reservoir, the microcapillary, or the reservoir and microcapillary; and
   an electric current generator configured to generate an electrophoretic flow through the microcapillary, where the electrophoretic flow is in opposition to the fluid flow, and where the electrophoretic flow is tuned to the fluid flow such that one or more types of particles present in the microcapillary migrate to a wall of the microcapillary and subsequently migrate against the fluid flow to a stagnation region,
   and wherein the microfluidic device has one or more step-changes in cross-sectional area in one or more areas across a length of the device.

* * * * *